(12) United States Patent
Denton et al.

(10) Patent No.: US 7,572,797 B2
(45) Date of Patent: Aug. 11, 2009

(54) AMINO SUBSTITUTED PYRAZINE DERIVATIVES FOR THE TREATMENT OF PAIN

(75) Inventors: Stephen Mark Denton, Sandwich (GB); Karl Richard Gibson, Sandwich (GB); Melanie Susanne Glossop, Sandwich (GB); Mark Ian Kemp, Sandwich (GB); Cedric Poinsard, Sandwich (GB)

(73) Assignee: Pfizer Inc., New York, NY (US)

( * ) Notice: Subject to any disclaimer, the term of this patent is extended or adjusted under 35 U.S.C. 154(b) by 341 days.

(21) Appl. No.: 11/556,354

(22) Filed: Nov. 3, 2006

(65) Prior Publication Data

US 2007/0105872 A1 May 10, 2007

Related U.S. Application Data

(60) Provisional application No. 60/733,662, filed on Nov. 4, 2005.

(51) Int. Cl.
*A61K 31/497* (2006.01)

(52) U.S. Cl. .................. 514/255.06; 544/405; 548/247; 548/373.1

(58) Field of Classification Search .................. 544/405
See application file for complete search history.

(56) References Cited

FOREIGN PATENT DOCUMENTS

| WO | WO 98/38174 A1 | 9/1998 |
|----|----------------|--------|
| WO | WO 03/045924 A1 | 6/2003 |
| WO | WO 03/051366 A2 | 6/2003 |

OTHER PUBLICATIONS

Akopian, et al., "The Tetrodtoxin-resistant Sodium Channel SNS has a Specialized Function in Pain Pathways" Nature Neuroscince, 1999, pp. 541-548, vol. 2, No. 6.
Akopian, et al., "a Tetrodtoxin-resistant Voltage-gated Sodium Channel Expressed by Sensory Neurons", Nature, 1996, pp. 257-262, vol. 379.
Black, et al., "Sensory Neuron-Specific Sodium Channel SNS is Abnormally Expressed in the Brains of Mice with Experimental Allergic Encephalomyelitis and Humans with Multiple Sclerosis", PNAS, 2000, pp. 11598-11602, vol. 97, No. 21.
Black, et al., "Abnormal expression of SNS/PN3 Sodium Channel in Cerebellar Purkinje Cells Following Loss of Myelin in the Taiep Rat", NeuroReport, 1999, pp. 913-918, vol. 10.
Bucknill, et al., "Nerve Finers in Lumbar Spine Structures and Injured Spinal Roots Express the Sensory Neuron=Specific Sodium Channels SNS/PN3 and NaN/SNS2", Spine, 2002, pp. 135-140, vol. 27, No. 2.
Coward, et al., :Immunolocalization of SNS/PN3 and NaN/SNS2 Sodium Channels in Human Pain States, Pain, 2000, pp. 41-50, vol. 85, No. 1-2.
Lai, et al., "Inihibition of Neuropathic Pain by Decreased Expression of the Tetrodotoxin-resistant Sodium Channel, NaV1.8", Pain, 2002, pp. 143-152, vol. 95.
Laird, et al., "Deficits in Visceral Pain and Referred Hyperalgesia in Nav1.8 (SNS/PN3)-Null Mice", J Neuroscience, 2992, pp. 8352-8356, vol. 22, No. 19.
Rabert, et al., "A Tetrodotoxin-resistant Voltage-gated Sodium Channel from Human Dorsal Root Ganglia, hPN3/SCN 10A", Pain, 1998, pp. 107-114, vol. 78, No. 2.
Shembalker, et al., "Increased Sodium Channel SNS/PN3 Immunoreactivity in a Causalgic Finger", Euro J Pain, 2001 pp. 319-323, vol. 5, No. 3.
Yiangou, et al., "SNS/PN3 and SNS2/NaN Sodium Channel-like Immunoreactivity in Human Adult and Neonate Injured Sensory Nerves", FEBS Letters, 2000, pp. 249-252, vol. 467, No. 2-3.

*Primary Examiner*—James O Wilson
*Assistant Examiner*—Brian McDowell
(74) *Attorney, Agent, or Firm*—Gregg C. Benson; A. Dean Olson

(57) ABSTRACT

The present invention relates to compounds of the formula

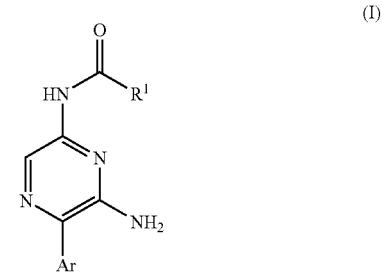

and pharmaceutically acceptable salts and solvates thereof, to processes for the preparation of, intermediates used in the preparation of, and compositions containing such compounds and the uses of such compounds for the treatment of pain.

10 Claims, No Drawings

AMINO SUBSTITUTED PYRAZINE DERIVATIVES FOR THE TREATMENT OF PAIN

This application is a United States utility application, which claims the benefit of priority to U.S. Provisional Application No. 60/733,662, filed Nov. 4, 2005.

This invention relates to pyrazine derivatives. More particularly, this invention relates to heteroaryl substituted N-[6-amino-5-aryl-pyrazin-2-yl]-carboxamide derivatives and to processes for the preparation of, intermediates used in the preparation of, compositions containing and the uses of, such derivatives.

The pyrazine derivatives of the present invention are sodium channel modulators and have a number of therapeutic applications, particularly in the treatment of pain. More particularly, the pyrazine derivatives of the invention are $Na_{V1.8}$ modulators. Preferred pyrazine derivatives of the invention show an affinity for the $Na_{V1.8}$ channel which is greater than their affinity for the tetrodotoxin-sensitive sodium channels (TTX-S). More preferred pyrazine derivatives of the invention show at least a 2-fold selectivity for the $Na_{V1.8}$ channel as compared with the tetrodotoxin-sensitive sodium channels, and most preferably an 8-fold selectivity.

The $Na_{V1.8}$ channel is a voltage-gated sodium channel which is expressed in nociceptors, the sensory neurones responsible for transducing painful stimuli. The rat channel and the human channel have been cloned in 1996 and 1998 respectively (*Nature* 1996; 379: 257-262; *Pain* 1998 (November); 78(2):107-114). The $Na_{V1.8}$ channel was previously known as SNS (sensory neurone specific) and PN3 (peripheral nerve type 3). The $Na_{V1.8}$ channel is atypical in that it shows resistance to the blocking effects of the puffer fish toxin tetrodotoxin and it is believed to underlie the slow-voltage-gated and tetrodotoxin-resistant (TTX-R) sodium currents recorded from dorsal root ganglion neurones. The closest molecular relative to the $Na_{V1.8}$ channel is the $Na_{V1.8}$ channel, which is the cardiac sodium channel, with which it shares approximately 60% homology. The $Na_{V1.8}$ channel is expressed most highly in the 'small cells' of the dorsal root ganglia (DRG). These are thought to be the C- and A-delta cells which are the putative polymodal nociceptors, or pain sensors. Under normal conditions, the $Na_{V1.8}$ channel is not expressed anywhere other than subpopulations of DRG neurones. The $Na_{V1.8}$ channels are thought to contribute to the process of DRG sensitisation and also to hyperexcitability due to nerve injury. Inhibitory modulation of the $Na_{V1.8}$ channels is aimed at reducing the excitability of nociceptors, by preventing them from contributing to the excitatory process.

Studies have shown that $Na_{V1.8}$ knock-out leads to a blunted pain phenotype, mostly to inflammatory challenges (A. N. Akopian et al., *Nat. Neurosci.* 1999; 2; 541-548) and that $Na_{V1.8}$ knockdown reduces pain behaviours, in this case neuropathic pain (J. Lai et al., *Pain,* 2002 (January); 95(1-2): 143-152). Coward et al. and Yiangou et al., have shown that $Na_{V1.8}$ appears to be expressed in pain conditions (*Pain.* 2000 (March); 85(1-2): 41-50 and FEBS Lett. 2000 (February 11); 467(2-3): 249-252). Laird et al., *J Neurosci.* 2002 (Oct. 1); 22(19): 8352-8356: Black et al., *Neuroreport.* 1999 (Apr. 6); 10(5): 913-918 and *Proc. Natl. Acad. Sci. USA* 2000: 97: 11598-11602).

Several sodium channel modulators are known for use as anticonvulsants or antidepressants, such as carbamazepine, amitriptyline, lamotrigine and riluzole, all of which target brain tetrodotoxin-sensitive (TTX-S) sodium channels. Such TTX-S agents suffer from dose-limiting side effects, including dizziness, ataxia and somnolence, primarily due to action at TTX-S channels in the brain.

WO-A-03/051366 discusses protein kinase inhibitors useful for the treatment of cancer. WO-A-03/45924 discusses $CRF_1$ antagonists useful for the treatment of CNS-related disorders. WO-A-98/38174 discusses pyrazine derivatives which are stated to act as sodium channel blockers.

It is an objective of the invention to provide new $Na_{V1.8}$ channel modulators that are good drug candidates. Preferred compounds should bind potently to the $Na_{V1.8}$ channel whilst showing little affinity for other sodium channels, particularly the TTX-S channels, and show functional activity as $Na_{V1.8}$ channel modulators. They should be well absorbed from the gastrointestinal tract, be metabolically stable and possess favourable pharmacokinetic properties. They should be non-toxic and demonstrate few side-effects. Furthermore, the ideal drug candidate will exist in a physical form that is stable, non-hygroscopic and easily formulated. Preferred pyrazine derivatives of the present invention are selective for the $Na_{V1.8}$ channel over the tetradotoxin-sensitive (TTX-S) sodium channels, leading to improvements in the side-effect profile.

The pyrazine derivatives of the present invention are therefore potentially useful in the treatment of a wide range of disorders, particularly pain, acute pain, chronic pain, neuropathic pain, inflammatory pain, visceral pain, nociceptive pain including post-surgical pain, and mixed pain types involving the viscera, gastrointestinal tract, cranial structures, musculoskeletal system, spine, urogenital system, cardiovascular system and CNS, including cancer pain, back and orofacial pain.

Other conditions that may be treated with the pyrazine derivatives of the present invention include multiple sclerosis, neurodegenerative disorders, irritable bowel syndrome, osteoarthritis, rheumatoid arthritis, neuropathological disorders, functional bowel disorders, inflammatory bowel diseases, pain associated with dysmenorrhea, pelvic pain, cystitis, pancreatitis, migraine, cluster and tension headaches, diabetic neuropathy, peripheral neuropathic pain, sciatica, fibromyalgia and causalgia.

The invention provides a pyrazine derivative of the formula (I):

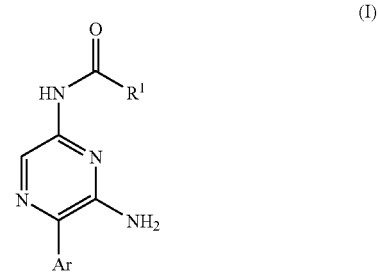

or a pharmaceutically acceptable salt or solvate thereof;

wherein $R^1$ is a 5-membered heteroaryl group comprising either (a) from 1 to 4 nitrogen atoms or (b) one oxygen or one sulphur atom and 0, 1 or 2 nitrogen atoms, optionally substituted by one or more substituents each independently selected from $(C_1-C_4)$alkyl, $(C_1-C_4)$alkoxy, halo$(C_1-C_4)$alkyl, $(C_1-C_4)$alkoxy$(C_1-C_4)$alkyl, amino$(C_1-C_4)$alkyl, amino, $(C_1-C_4)$alkylamino, di-$((C_1-C_4)$alkyl)amino, $(C_1-C_4)$alkylamino$(C_1-C_4)$alkyl and di-$((C_1-C_4)$alkyl)amino$(C_1-C_4)$alkyl; with the proviso that $R^1$ is not imidazolyl, oxazolyl or 1,2,4-triazolyl;

Ar is

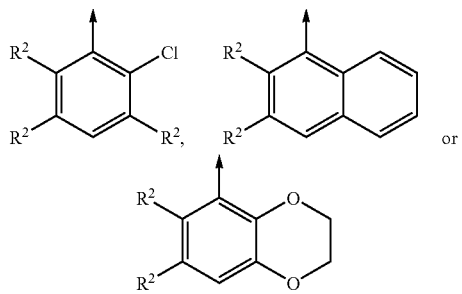

wherein → indicates the point of attachment to the pyrazine ring; and each $R^2$ is independently selected from hydrogen, $(C_1-C_4)$ alkyl, $(C_1-C_4)$alkoxy, halo$(C_1-C_4)$alkyl, halo$(C_1-C_4)$alkoxy, cyano and halo.

In the above definitions, halo means fluoro, chloro, bromo or iodo. Alkyl, and alkoxy groups, containing the requisite number of carbon atoms, can be unbranched or branched. Examples of alkyl include methyl, ethyl, n-propyl, i-propyl, n-butyl, i-butyl, sec-butyl and t-butyl. Examples of alkoxy include methoxy, ethoxy, n-propoxy, i-propoxy, n-butoxy, i-butoxy, sec-butoxy and t-butoxy. Examples of haloalkyl include trifluoromethyl.

Specific examples of $R^1$ include thienyl, furanyl, pyrrolyl, pyrazolyl, isoxazolyl, thiazolyl, isothiazolyl, 1,2,3-triazolyl, oxadiazolyl, thiadiazolyl and tetrazolyl (each optionally substituted as specified above).

In a preferred aspect (A), the invention provides a pyrazine derivative of the formula (I), or a pharmaceutically acceptable salt or solvate thereof, wherein Ar is

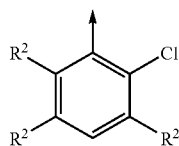

and $R^1$ and $R^2$ are as defined above; more preferably, Ar is 2-chlorophenyl, 2,3-dichlorophenyl, 2,5-dichlorophenyl, 2,5-dichloro-3-methoxyphenyl, 2,3,5-trichlorophenyl, 2-chloro-5-methoxyphenyl, 2,3-dichloro-5-methoxyphenyl or 2-chloro-5-cyanophenyl.

In a preferred aspect (B), the invention provides a pyrazine derivative of the formula (I), or a pharmaceutically acceptable salt or solvate thereof, wherein Ar is as defined above, either in its broadest aspect or in a preferred aspect under (A); and $R^1$ is pyrazolyl or isoxazolyl, each being optionally substituted with $(C_1-C_4)$alkyl or $(C_1-C_4)$alkoxy$(C_1-C_4)$alkyl; more preferably $R^1$ is pyrazolyl or isoxazolyl, each being substituted with one, two or three substituents independently selected from methyl, ethyl, and isopropyl; individual preferred $R^1$ groups are 3-methylisoxazol-4-yl, 1-methyl-1H-pyrazol-5-yl, 5-isopropylisoxazol-4-yl, 5-methylisoxazol-4-yl or 3-ethyl-5-methyl-isoxazol-4-yl.

In a preferred aspect (C), the invention provides a pyrazine derivative of the formula (I), or a pharmaceutically acceptable salt or solvate thereof, wherein Ar and $R^1$ are as defined above, either in their broadest aspects or in a preferred aspect under (A) or (B), and each $R^2$ is independently selected from hydrogen, methoxy, ethoxy, cyano, methyl, ethyl, trifluoromethyl, trifluomethoxy, chloro and fluoro; more preferably each $R^2$ is independently selected from hydrogen, methoxy, cyano, trifluoromethyl, chloro and fluoro.

Specific preferred pyrazine derivatives according to the invention are those listed in the Examples section below and the pharmaceutically acceptable salts and solvates thereof. Even more preferred pyrazine derivatives according to the invention are those compounds selected from:

N-[6-amino-5-(2,3-dichlorophenyl)pyrazin-2-yl]-3-methyl-isoxazole-4-carboxamide;

N-[6-amino-5-(2,5-dichlorophenyl)pyrazin-2-yl]-3-methyl-isoxazole-4-carboxamide;

N-[6-amino-5-(2,5-dichloro-3-methoxyphenyl)pyrazin-2-yl]-3-methylisoxazole-4-carboxamide;

N-[6-amino-5-(2,3-dichloro-5-methoxyphenyl)pyrazin-2-yl]-1-methyl-1H-pyrazole-5-carboxamide;

N-[6-amino-5-(2-chlorophenyl)pyrazin-2-yl]-5-isopropyl-isoxazole-4-carboxamide;

N-[6-amino-5-(2-chlorophenyl)pyrazin-2-yl]-3-methylisoxazole-4-carboxamide;

N-[6-amino-5-(2,3,5-trichlorophenyl)pyrazin-2-yl]-5-methylisoxazole-4-carboxamide;

N-[6-amino-5-(2-chloro-5-methoxyphenyl)pyrazin-2-yl]-3-methylisoxazole-4-carboxamide;

N-[6-amino-5-(2-chloro-5-cyanophenyl)pyrazin-2-yl]-1-methyl-1H-pyrazole-5-carboxamide;

N-[6-amino-5-(2-chloro-5-methoxyphenyl)pyrazin-2-yl]-3-ethyl-5-methylisoxazole-4-carboxamide;

N-[6-amino-5-(2-chloro-5-methoxyphenyl)pyrazin-2-yl]-1-methyl-1H-pyrazole-5-carboxamide;

N-[6-amino-5-(2,5-dichlorophenyl)pyrazin-2-yl]-1-methyl-1H-pyrazole-5-carboxamide; and N-[6-amino-5-(2-chloro-5-methoxphenyl)pyrazin-2-yl]-5-isopropylisoxazole-4-carboxamide;

and the pharmaceutically acceptable salts or solvates thereof.

The compounds of formula (I), being $Na_{V1.8}$ channel modulators, are potentially useful in the treatment of a range of disorders. The treatment of pain, particularly chronic, inflammatory, neuropathic, nociceptive and visceral pain, is a preferred use.

Physiological pain is an important protective mechanism designed to warn of danger from potentially injurious stimuli from the external environment. The system operates through a specific set of primary sensory neurones and is activated by noxious stimuli via peripheral transducing mechanisms (see Millan, 1999, Prog. Neurobiol., 57, 1-164 for a review). These sensory fibres are known as nociceptors and are characteristically small diameter axons with slow conduction velocities. Nociceptors encode the intensity, duration and quality of noxious stimulus and by virtue of their topographically organised projection to the spinal cord, the location of the stimulus. The nociceptors are found on nociceptive nerve fibres of which there are two main types, A-delta fibres (myelinated) and C fibres (non-myelinated). The activity generated by nociceptor input is transferred, after complex processing in the dorsal horn, either directly, or via brain stem relay nuclei, to the ventrobasal thalamus and then on to the cortex, where the sensation of pain is generated.

Pain may generally be classified as acute or chronic. Acute pain begins suddenly and is short-lived (usually twelve weeks or less). It is usually associated with a specific cause such as a specific injury and is often sharp and severe. It is the kind of pain that can occur after specific injuries resulting from surgery, dental work, a strain or a sprain. Acute pain does not generally result in any persistent psychological response. In contrast, chronic pain is long-term pain, typically persisting for more than three months and leading to significant psychological and emotional problems. Common examples of chronic pain are neuropathic pain (e.g. painful diabetic neuropathy, postherpetic neuralgia), carpal tunnel syndrome, back pain, headache, cancer pain, arthritic pain and chronic post-surgical pain.

When a substantial injury occurs to body tissue, via disease or trauma, the characteristics of nociceptor activation are altered and there is sensitisation in the periphery, locally around the injury and centrally where the nociceptors terminate. These effects lead to a heightened sensation of pain. In acute pain these mechanisms can be useful, in promoting protective behaviours which may better enable repair processes to take place. The normal expectation would be that sensitivity returns to normal once the injury has healed. However, in many chronic pain states, the hypersensitivity far outlasts the healing process and is often due to nervous system injury. This injury often leads to abnormalities in sensory nerve fibres associated with maladaptation and aberrant activity (Woolf & Salter, 2000, Science, 288, 1765-1768).

Clinical pain is present when discomfort and abnormal sensitivity feature among the patient's symptoms. Patients tend to be quite heterogeneous and may present with various pain symptoms. Such symptoms include: 1) spontaneous pain which may be dull, burning, or stabbing; 2) exaggerated pain responses to noxious stimuli (hyperalgesia); and 3) pain produced by normally innocuous stimuli (allodynia—Meyer et al., 1994, Textbook of Pain, 13-44). Although patients suffering from various forms of acute and chronic pain may have similar symptoms, the underlying mechanisms may be different and may, therefore, require different treatment strategies. Pain can also therefore be divided into a number of different subtypes according to differing pathophysiology, including nociceptive, inflammatory and neuropathic pain.

Nociceptive pain is induced by tissue injury or by intense stimuli with the potential to cause injury. Pain afferents are activated by transduction of stimuli by nociceptors at the site of injury and activate neurons in the spinal cord at the level of their termination. This is then relayed up the spinal tracts to the brain where pain is perceived (Meyer et al., 1994, Textbook of Pain, 13-44). The activation of nociceptors activates two types of afferent nerve fibres. Myelinated A-delta fibres transmit rapidly and are responsible for sharp and stabbing pain sensations, whilst unmyelinated C fibres transmit at a slower rate and convey a dull or aching pain. Moderate to severe acute nociceptive pain is a prominent feature of pain from central nervous system trauma, strains/sprains, burns, myocardial infarction and acute pancreatitis, post-operative pain (pain following any type of surgical procedure), post-traumatic pain, renal colic, cancer pain and back pain. Cancer pain may be chronic pain such as tumour related pain (e.g. bone pain, headache, facial pain or visceral pain) or pain associated with cancer therapy (e.g. postchemotherapy syndrome, chronic postsurgical pain syndrome or post radiation syndrome). Cancer pain may also occur in response to chemotherapy, immunotherapy, hormonal therapy or radiotherapy. Back pain may be due to herniated or ruptured intervertebral discs or abnormalities of the lumber facet joints, sacroiliac joints, paraspinal muscles or the posterior longitudinal ligament. Back pain may resolve naturally but in some patients, where it lasts over 12 weeks, it becomes a chronic condition which can be particularly debilitating.

Neuropathic pain is currently defined as pain initiated or caused by a primary lesion or dysfunction in the nervous system. Nerve damage can be caused by trauma and disease and thus the term 'neuropathic pain' encompasses many disorders with diverse aetiologies. These include, but are not limited to, peripheral neuropathy, diabetic neuropathy, post herpetic neuralgia, trigeminal neuralgia, back pain, cancer neuropathy, HIV neuropathy, phantom limb pain, carpal tunnel syndrome, central post-stroke pain and pain associated with chronic alcoholism, hypothyroidism, uremia, multiple sclerosis, spinal cord injury, Parkinson's disease, epilepsy and vitamin deficiency. Neuropathic pain is pathological as it has no protective role. It is often present well after the original cause has dissipated, commonly lasting for years, significantly decreasing a patient's quality of life (Woolf and Mannion, 1999, Lancet, 353, 1959-1964). The symptoms of neuropathic pain are difficult to treat, as they are often heterogeneous even between patients with the same disease (Woolf & Decosterd, 1999, Pain Supp., 6, S141-S147; Woolf and Mannion, 1999, Lancet, 353, 1959-1964). They include spontaneous pain, which can be continuous, and paroxysmal or abnormal evoked pain, such as hyperalgesia (increased sensitivity to a noxious stimulus) and allodynia (sensitivity to a normally innocuous stimulus).

The inflammatory process is a complex series of biochemical and cellular events, activated in response to tissue injury or the presence of foreign substances, which results in swelling and pain (Levine and Taiwo, 1994, Textbook of Pain, 45-56). Arthritic pain is the most common inflammatory pain. Rheumatoid disease is one of the commonest chronic inflammatory conditions in developed countries and rheumatoid arthritis is a common cause of disability. The exact aetiology of rheumatoid arthritis is unknown, but current hypotheses suggest that both genetic and microbiological factors may be important (Grennan & Jayson, 1994, Textbook of Pain, 397-407). It has been estimated that almost 16 million Americans have symptomatic osteoarthritis (OA) or degenerative joint disease, most of whom are over 60 years of age, and this is expected to increase to 40 million as the age of the population increases, making this a public health problem of enormous magnitude (Houge & Mersfelder, 2002, Ann Pharmacother., 36, 679-686; McCarthy et al., 1994, Textbook of Pain, 387-395). Most patients with osteoarthritis seek medical attention because of the associated pain. Arthritis has a significant impact on psychosocial and physical function and is known to be the leading cause of disability in later life. Ankylosing spondylitis is also a rheumatic disease that causes arthritis of the spine and sacroiliac joints. It varies from intermittent episodes of back pain that occur throughout life to a severe chronic disease that attacks the spine, peripheral joints and other body organs.

Another type of inflammatory pain is visceral pain which includes pain associated with inflammatory bowel disease (IBD). Visceral pain is pain associated with the viscera, which encompass the organs of the abdominal cavity. These organs include the sex organs, spleen and part of the digestive system. Pain associated with the viscera can be divided into digestive visceral pain and non-digestive visceral pain. Commonly encountered gastrointestinal (GI) disorders that cause pain include functional bowel disorder (FBD) and inflammatory bowel disease (IBD). These GI disorders include a wide range of disease states that are currently only moderately controlled, including, in respect of FBD, gastroesophageal reflux, dyspepsia, irritable bowel syndrome (IBS) and functional abdominal pain syndrome (FAPS), and, in respect of IBD, Crohn's disease, ileitis and ulcerative colitis, all of which regularly produce visceral pain. Other types of visceral pain include the pain associated with dysmenorrhea, cystitis and pancreatitis and pelvic pain.

It should be noted that some types of pain have multiple aetiologies and thus can be classified in more than one area, e.g. back pain and cancer pain have both nociceptive and neuropathic components.

Other types of pain include:

pain resulting from musculo-skeletal disorders, including myalgia, fibromyalgia, spondylitis, sero-negative (non-rheumatoid) arthropathies, non-articular rheumatism, dystrophinopathy, glycogenolysis, polymyositis and pyomyositis;

heart and vascular pain, including pain caused by angina, myocardical infarction, mitral stenosis, pericarditis, Raynaud's phenomenon, scleredoma and skeletal muscle ischemia;

head pain, such as migraine (including migraine with aura and migraine without aura), cluster headache, tension-type headache mixed headache and headache associated with vascular disorders; and orofacial pain, including dental pain, otic pain, burning mouth syndrome and temporomandibular myofascial pain.

The pyrazine derivatives of formula (I) are also expected to be useful in the treatment of multiple sclerosis.

The invention also relates to therapeutic use of the pyrazine derivatives of formula (I) as agents for treating or relieving the symptoms of neurodegenerative disorders. Such neurodegenerative disorders include, for example, Alzheimer's disease, Huntington's disease, Parkinson's disease, and Amyotrophic Lateral Sclerosis. The present invention also covers treating neurodegenerative disorders termed acute brain injury. These include but are not limited to: stroke, head trauma, and asphyxia. Stroke refers to a cerebral vascular disease and may also be referred to as a cerebral vascular accident (CVA) and includes acute thromboembolic stroke. Stroke includes both focal and global ischemia. Also, included are transient cerebral ischemic attacks and other cerebral vascular problems accompanied by cerebral ischemia. These vascular disorders may occur in a patient undergoing carotid endarterectomy specifically or other cerebrovascular or vascular surgical procedures in general, or diagnostic vascular procedures including cerebral angiography and the like. Other incidents are head trauma, spinal cord trauma, or injury from general anoxia, hypoxia, hypoglycemia, hypotension as well as similar injuries seen during procedures from embole, hyperfusion, and hypoxia. The instant invention would be useful in a range of incidents, for example, during cardiac bypass surgery, in incidents of intracranial hemorrhage, in perinatal asphyxia, in cardiac arrest, and status epilepticus.

A skilled physician will be able to determine the appropriate situation in which subjects are susceptible to or at risk of, for example, stroke as well as suffering from stroke for administration by methods of the present invention.

Pharmaceutically acceptable salts of the compounds of formula (I) include the acid addition and base salts thereof.

Suitable acid addition salts are formed from acids which form non-toxic salts. Examples include the acetate, adipate, aspartate, benzoate, besylate, bicarbonate/carbonate, bisulphate/sulphate, borate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, pyroglutamate, saccharate, stearate, succinate, tannate, tartrate, tosylate, trifluoroacetate and xinofoate salts.

Suitable base salts are formed from bases which form non-toxic salts. Examples include the aluminium, arginine, benzathine, calcium, choline, diethylamine, diolamine, glycine, lysine, magnesium, meglumine, olamine, potassium, sodium, tromethamine and zinc salts.

Hemisalts of acids and bases may also be formed, for example, hemisulphate and hemicalcium salts.

For a review on suitable salts, see *Handbook of Pharmaceutical Salts: Properties, Selection, and Use* by Stahl and Wermuth (Wiley-VCH, 2002).

Pharmaceutically acceptable salts of compounds of formula (I) may be prepared by one or more of three methods:

(i) by reacting the compound of formula (I) with the desired acid or base;

(ii) by removing an acid- or base-labile protecting group from a suitable precursor of the compound of formula (I); or (iii) by converting one salt of the compound of formula (I) to another by reaction with an appropriate acid or base or by means of a suitable ion exchange column.

All three reactions are typically carried out in solution. The resulting salt may precipitate out and be collected by filtration or may be recovered by evaporation of the solvent. The degree of ionisation in the resulting salt may vary from completely ionised to almost non-ionised.

The compounds of the invention may exist in a continuum of solid states ranging from fully amorphous to fully crystalline. The term 'amorphous' refers to a state in which the material lacks long range order at the molecular level and, depending upon temperature, may exhibit the physical properties of a solid or a liquid. Typically such materials do not give distinctive X-ray diffraction patterns and, while exhibiting the properties of a solid, are more formally described as a liquid. Upon heating, a change from solid to liquid properties occurs which is characterised by a change of state, typically second order ('glass transition'). The term 'crystalline' refers to a solid phase in which the material has a regular ordered internal structure at the molecular level and gives a distinctive X-ray diffraction pattern with defined peaks. Such materials when heated sufficiently will also exhibit the properties of a liquid, but the change from solid to liquid is characterised by a phase change, typically first order ('melting point').

The compounds of the invention may also exist in unsolvated and solvated forms. The term 'solvate' is used herein to describe a molecular complex comprising the compound of the invention and one or more pharmaceutically acceptable solvent molecules, for example, ethanol. The term 'hydrate' is employed when said solvent is water.

A currently accepted classification system for organic hydrates is one that defines isolated site, channel, or metal-ion coordinated hydrates—see *Polymorphism in Pharmaceutical Solids* by K. R. Morris (Ed. H. G. Brittain, Marcel Dekker, 1995). Isolated site hydrates are ones in which the water molecules are isolated from direct contact with each other by intervening organic molecules. In channel hydrates, the water molecules lie in lattice channels where they are next to other water molecules. In metal-ion coordinated hydrates, the water molecules are bonded to the metal ion.

When the solvent or water is tightly bound, the complex will have a well-defined stoichiometry independent of humidity. When, however, the solvent or water is weakly bound, as in channel solvates and hygroscopic compounds, the water/solvent content will be dependent on humidity and drying conditions. In such cases, non-stoichiometry will be the norm.

Also included within the scope of the invention are multi-component complexes (other than salts and solvates) wherein the drug and at least one other component are present in stoichiometric or non-stoichiometric amounts. Complexes of this type include clathrates (drug-host inclusion complexes) and co-crystals. The latter are typically defined as crystalline complexes of neutral molecular constituents which are bound together through non-covalent interactions, but could also be a complex of a neutral molecule with a salt. Co-crystals may be prepared by melt crystallisation, by recrystallisation from solvents, or by physically grinding the components together—see Chem Commun, 17, 1889-1896, by O. Almarsson and M. J. Zaworotko (2004). For a general review of multi-component complexes, see J Pharm Sci, 64 (8), 1269-1288, by Haleblian (August 1975).

The compounds of the invention may also exist in a mesomorphic state (mesophase or liquid crystal) when subjected to suitable conditions. The mesomorphic state is intermediate between the true crystalline state and the true liquid state (either melt or solution). Mesomorphism arising as the result of a change in temperature is described as 'thermotropic' and that resulting from the addition of a second component, such as water or another solvent, is described as 'lyotropic'. Compounds that have the potential to form lyotropic mesophases are described as 'amphiphilic' and consist of molecules which possess an ionic (such as —COO$^-$Na$^+$, —COO$^-$K$^+$, or —SO$_3$$^-$Na$^+$) or non-ionic (such as —N$^-$N$^+$(CH$_3$)$_3$) polar head group. For more information, see *Crystals and the Polarizing Microscope* by N. H. Hartshorne and A. Stuart, 4$^{th}$ Edition (Edward Arnold, 1970).

Hereinafter all references to compounds of formula (i) include references to salts, solvates, multi-component complexes and liquid crystals thereof and to solvates, multi-component complexes and liquid crystals of salts thereof.

The compounds of the invention include compounds of formula (I) as hereinbefore defined, including all polymorphs and crystal habits thereof, prodrugs and isomers thereof (including optical, geometric and tautomeric isomers) as hereinafter defined and isotopically-labeled compounds of formula (I).

As indicated, so-called 'prodrugs' of the compounds of formula (I) are also within the scope of the invention. Thus certain derivatives of compounds of formula (I) which may have little or no pharmacological activity themselves can, when administered into or onto the body, be converted into compounds of formula (I) having the desired activity, for example, by hydrolytic cleavage. Such derivatives are referred to as 'prodrugs'. Further information on the use of prodrugs may be found in *Pro-drugs as Novel Delivery Systems*, Vol. 14, ACS Symposium Series (T. Higuchi and W. Stella) and *Bioreversible Carriers in Drug Design*, Pergamon Press, 1987 (Ed. E. B. Roche, American Pharmaceutical Association).

Prodrugs in accordance with the invention can, for example, be produced by replacing appropriate functionalities present in the compounds of formula (I) with certain moieties known to those skilled in the art as 'pro-moieties' as described, for example, in *Design of Prodrugs* by H. Bundgaard (Elsevier, 1985).

Some examples of prodrugs in accordance with the invention include where the compound of formula (I) contains a primary or secondary amino functionality (—NH$_2$ or —NHR where R≠H), an amide thereof, for example, a compound wherein, as the case may be, one or both hydrogens of the amino functionality of the compound of formula (I) is/are replaced by (C$_1$-C$_{10}$)alkanoyl.

Further examples of replacement groups in accordance with the foregoing examples and examples of other prodrug types may be found in the aforementioned references.

Moreover, certain compounds of formula (I) may themselves act as prodrugs of other compounds of formula (I).

Also included within the scope of the invention are metabolites of compounds of formula (I), that is, compounds formed in vivo upon administration of the drug. Some examples of metabolites in accordance with the invention include
(i) where the compound of formula (I) contains a methyl group, an hydroxymethyl derivative thereof (—CH$_3$->—CH$_2$OH):
(ii) where the compound of formula (I) contains an alkoxy group, an hydroxy derivative thereof (—OR->—OH);
(iii) where the compound of formula (I) contains a secondary amino group, a primary derivative thereof (—NHR$^1$->—NH$_2$);
(iv) where the compound of formula (I) contains a phenyl moiety, a phenol derivative thereof (—Ph->—PhOH); and Compounds of formula (I) containing one or more asymmetric carbon atoms can exist as two or more stereoisomers. Where structural isomers are interconvertible via a low energy barrier, tautomeric isomerism ('tautomerism') can occur. This can take the form of so-called valence tautomerism in compounds which contain an aromatic moiety. It follows that a single compound may exhibit more than one type of isomerism. Included within the scope of the present invention are all stereoisomers and tautomeric forms of the compounds of formula (I), including compounds exhibiting more than one type of isomerism, and mixtures of one or more thereof. Also included are acid addition or base salts wherein the counterion is optically active, for example, d-lactate or l-lysine, or racemic, for example, dl-tartrate or dl-arginine.

Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC).

Alternatively, the racemate (or a racemic precursor) may be reacted with a suitable optically active compound, for example, an alcohol, or, in the case where the compound of formula (I) contains an acidic or basic moiety, a base or acid such as 1-phenylethylamine or tartaric acid. The resulting diastereomeric mixture may be separated by chromatography and/or fractional crystallization and one or both of the diastereoisomers converted to the corresponding pure enantiomer(s) by means well known to a skilled person.

Chiral compounds of the invention (and chiral precursors thereof) may be obtained in enantiomerically-enriched form using chromatography, typically HPLC, on an asymmetric resin with a mobile phase consisting of a hydrocarbon, typically heptane or hexane, containing from 0 to 50% by volume of isopropanol, typically from 2% to 20%, and from 0 to 5% by volume of an alkylamine, typically 0.1% diethylamine. Concentration of the eluate affords the enriched mixture.

When any racemate crystallises, crystals of two different types are possible. The first type is the racemic compound (true racemate) referred to above wherein one homogeneous form of crystal is produced containing both enantiomers in equimolar amounts. The second type is the racemic mixture or conglomerate wherein two forms of crystal are produced in equimolar amounts each comprising a single enantiomer.

While both of the crystal forms present in a racemic mixture have identical physical properties, they may have different physical properties compared to the true racemate. Racemic mixtures may be separated by conventional techniques known to those skilled in the art—see, for example, *Stereochemistry of Organic Compounds* by E. L. Eliel and S. H. Wilen (Wiley, 1994).

The present invention includes all pharmaceutically acceptable isotopically-labelled compounds of formula I wherein one or more atoms are replaced by atoms having the same atomic number, but an atomic mass or mass number different from the atomic mass or mass number which predominates in nature.

Examples of isotopes suitable for inclusion in the compounds of the invention include isotopes of hydrogen, such as $^2$H and $^3$H, carbon, such as $^{11}$C, $^{13}$C and $^{14}$C, chlorine, such as $^{36}$Cl, fluorine, such as $^{18}$F, iodine, such as $^{123}$I and $^{125}$I nitrogen, such as $^{13}$N and $^{15}$N, oxygen, such as $^{15}$O, $^{17}$O and $^{18}$O, phosphorus, such as $^{32}$P, and sulphur, such as $^{35}$S.

Certain isotopically-labelled compounds of formula (I), for example, those incorporating a radioactive isotope, are useful in drug and/or substrate tissue distribution studies. The radioactive isotopes tritium, i.e. $^3$H, and carbon-14, i.e. $^{14}$C, are particularly useful for this purpose in view of their ease of incorporation and ready means of detection.

Substitution with heavier isotopes such as deuterium, ie. $^2$H, may afford certain therapeutic advantages resulting from greater metabolic stability, for example, increased in vivo half-life or reduced dosage requirements, and hence may be preferred in some circumstances.

Substitution with positron emitting isotopes, such as $^{11}$C, $^{18}$F, $^{15}$O and $^{13}$N, can be useful in Positron Emission Topography (PET) studies for examining substrate receptor occupancy.

Isotopically-labeled compounds of formula (I) can generally be prepared by conventional techniques known to those skilled in the art or by processes analogous to those described in the accompanying Examples and Preparations using an appropriate isotopically-labeled reagent in place of the non-labeled reagent previously employed.

Pharmaceutically acceptable solvates in accordance with the invention include those wherein the solvent of crystallization may be isotopically substituted, e.g. $D_2O$, $d_6$-acetone, $d_6$-DMSO.

Also within the scope of the invention are novel intermediate compounds as defined below, all salts, solvates and complexes thereof and all solvates and complexes of salts thereof as defined hereinbefore for compounds of formula (I). The invention includes all polymorphs of the aforementioned species and crystal habits thereof.

The compounds of formula (I) should be assessed for their biopharmaceutical properties, such as solubility and solution stability (across pH), permeability, etc., in order to select the most appropriate dosage form and route of administration for treatment of the proposed indication.

Compounds of the invention intended for pharmaceutical use may be administered as crystalline or amorphous products. They may be obtained, for example, as solid plugs, powders, or films by methods such as precipitation, crystallization, freeze drying, spray drying, or evaporative drying. Microwave or radio frequency drying may be used for this purpose.

They may be administered alone or in combination with one or more other compounds of the invention or in combination with one or more other drugs (or as any combination thereof). Generally, they will be administered as a formulation in association with one or more pharmaceutically acceptable excipients. The term 'excipient' is used herein to describe any ingredient other than the compound(s) of the invention. The choice of excipient will to a large extent depend on factors such as the particular mode of administration, the effect of the excipient on solubility and stability, and the nature of the dosage form.

Pharmaceutical compositions suitable for the delivery of compounds of the present invention and methods for their preparation will be readily apparent to those skilled in the art. Such compositions and methods for their preparation may be found, for example, in *Remington's Pharmaceutical Sciences,* 19th Edition (Mack Publishing Company, 1995).

The compounds of the invention may be administered orally. Oral administration may involve swallowing, so that the compound enters the gastrointestinal tract, and/or buccal, lingual, or sublingual administration by which the compound enters the blood stream directly from the mouth.

Formulations suitable for oral administration include solid, semi-solid and liquid systems such as tablets; soft or hard capsules containing multi- or nano-particulates, liquids, or powders; lozenges (including liquid-filled); chews; gels; fast dispersing dosage forms; films; ovules; sprays; and buccal/mucoadhesive patches.

Liquid formulations include suspensions, solutions, syrups and elixirs. Such formulations may be employed as fillers in soft or hard capsules (made, for example, from gelatin or hydroxypropylmethylcellulose) and typically comprise a carrier, for example, water, ethanol, polyethylene glycol, propylene glycol, methylcellulose, or a suitable oil, and one or more emulsifying agents and/or suspending agents. Liquid formulations may also be prepared by the reconstitution of a solid, for example, from a sachet.

The compounds of the invention may also be used in fast-dissolving, fast-disintegrating dosage forms such as those described in Expert Opinion in Therapeutic Patents, 11 (6), 981-986, by Liang and Chen (2001).

For tablet dosage forms, depending on dose, the drug may make up from 1 weight % to 80 weight % of the dosage form, more typically from 5 weight % to 60 weight % of the dosage form. In addition to the drug, tablets generally contain a disintegrant. Examples of disintegrants include sodium starch glycolate, sodium carboxymethyl cellulose, calcium carboxymethyl cellulose, croscarmellose sodium, crospovidone, polyvinylpyrrolidone, methyl cellulose, microcrystalline cellulose, lower alkyl-substituted hydroxypropyl cellulose, starch, pregelatinised starch and sodium alginate. Generally, the disintegrant will comprise from 1 weight % to 25 weight %, preferably from 5 weight % to 20 weight % of the dosage form.

Binders are generally used to impart cohesive qualities to a tablet formulation. Suitable binders include microcrystalline cellulose, gelatin, sugars, polyethylene glycol, natural and synthetic gums, polyvinylpyrrolidone, pregelatinised starch, hydroxypropyl cellulose and hydroxypropyl methylcellulose. Tablets may also contain diluents, such as lactose (monohydrate, spray-dried monohydrate, anhydrous and the like), mannitol, xylitol, dextrose, sucrose, sorbitol, microcrystalline cellulose, starch and dibasic calcium phosphate dihydrate.

Tablets may also optionally comprise surface active agents, such as sodium lauryl sulfate and polysorbate 80, and glidants such as silicon dioxide and talc. When present, surface active agents may comprise from 0.2 weight % to 5 weight % of the tablet, and glidants may comprise from 0.2 weight % to 1 weight % of the tablet.

Tablets also generally contain lubricants such as magnesium stearate, calcium stearate, zinc stearate, sodium stearyl fumarate, and mixtures of magnesium stearate with sodium lauryl sulphate. Lubricants generally comprise from 0.25 weight % to 10 weight %, preferably from 0.5 weight % to 3 weight % of the tablet.

Other possible ingredients include anti-oxidants, colourants, flavouring agents, preservatives and taste-masking agents.

Exemplary tablets contain up to about 80% drug, from about 10 weight % to about 90 weight % binder, from about 0 weight % to about 85 weight % diluent, from about 2 weight % to about 10 weight % disintegrant, and from about 0.25 weight % to about 10 weight % lubricant.

Tablet blends may be compressed directly or by roller to form tablets. Tablet blends or portions of blends may alternatively be wet-, dry-, or melt-granulated, melt congealed, or extruded before tabletting. The final formulation may comprise one or more layers and may be coated or uncoated; it may even be encapsulated.

The formulation of tablets is discussed in *Pharmaceutical Dosage Forms: Tablets*, Vol. 1, by H. Lieberman and L. Lachman (Marcel Dekker, New York, 1980).

Consumable oral films for human or veterinary use are typically pliable water-soluble or water-swellable thin film dosage forms which may be rapidly dissolving or mucoadhesive and typically comprise a compound of formula (I), a film-forming polymer, a binder, a solvent, a humectant, a plasticiser, a stabiliser or emulsifier, a viscosity-modifying agent and a solvent. Some components of the formulation may perform more than one function.

The compound of formula (I) may be water-soluble or insoluble. A water-soluble compound typically comprises from 1 weight % to 80 weight %, more typically from 20 weight % to 50 weight %, of the solutes. Less soluble compounds may comprise a greater proportion of the composition, typically up to 88 weight % of the solutes. Alternatively, the compound of formula (I) may be in the form of multiparticulate beads.

The film-forming polymer may be selected from natural polysaccharides, proteins, or synthetic hydrocolloids and is typically present in the range 0.01 to 99 weight %, more typically in the range 30 to 80 weight %.

Other possible ingredients include anti-oxidants, colorants, flavourings and flavour enhancers, preservatives, salivary stimulating agents, cooling agents, co-solvents (including oils), emollients, bulking agents, anti-foaming agents, surfactants and taste-masking agents.

Films in accordance with the invention are typically prepared by evaporative drying of thin aqueous films coated onto a peelable backing support or paper. This may be done in a drying oven or tunnel, typically a combined coater dryer, or by freeze-drying or vacuuming.

Solid formulations for oral administration may be formulated to be immediate and/or modified release. Modified release formulations include delayed-, sustained-, pulsed-, controlled-, targeted and programmed release.

Suitable modified release formulations for the purposes of the invention are described in U.S. Pat. No. 6,106,864. Details of other suitable release technologies such as high energy dispersions and osmotic and coated particles are to be found in *Pharmaceutical Technology On-line*, 25(2), 1-14, by Verma et al (2001). The use of chewing gum to achieve controlled release is described in WO 00/35298.

The compounds of the invention may also be administered directly into the blood stream, into muscle, or into an internal organ. Suitable means for parenteral administration include intravenous, intraarterial, intraperitoneal, intrathecal, intraventricular, intraurethral, intrasternal, intracranial, intramuscular, intrasynovial and subcutaneous. Suitable devices for parenteral administration include needle (including microneedle) injectors, needle-free injectors and infusion techniques.

Parenteral formulations are typically aqueous solutions which may contain excipients such as salts, carbohydrates and buffering agents (preferably to a pH of from 3 to 9), but, for some applications, they may be more suitably formulated as a sterile non-aqueous solution or as a dried form to be used in conjunction with a suitable vehicle such as sterile, pyrogen-free water.

The preparation of parenteral formulations under sterile conditions, for example, by lyophilisation, may readily be accomplished using standard pharmaceutical techniques well known to those skilled in the art.

The solubility of compounds of formula (I) used in the preparation of parenteral solutions may be increased by the use of appropriate formulation techniques, such as the incorporation of solubility-enhancing agents.

Formulations for parenteral administration may be formulated to be immediate and/or modified release. Modified release formulations include delayed-, sustained-, pulsed-, controlled-, targeted and programmed release. Thus compounds of the invention may be formulated as a suspension or as a solid, semi-solid, or thixotropic liquid for administration as an implanted depot providing modified release of the active compound. Examples of such formulations include drug-coated stents and semi-solids and suspensions comprising drug-loaded poly(dl-lactic-coglycolic)acid (PGLA) microspheres.

The compounds of the invention may also be administered topically, (intra)dermally, or transdermally to the skin or mucosa. Typical formulations for this purpose include gels, hydrogels, lotions, solutions, creams, ointments, dusting powders, dressings, foams, films, skin patches, wafers, implants, sponges, fibres, bandages and microemulsions. Liposomes may also be used. Typical carriers include alcohol, water, mineral oil, liquid petrolatum, white petrolatum, glycerin, polyethylene glycol and propylene glycol. Penetration enhancers may be incorporated—see, for example, J Pharm Sci, 88 (10), 955-958, by Finnin and Morgan (October 1999).

Other means of topical administration include delivery by electroporation, iontophoresis, phonophoresis, sonophoresis and microneedle or needle-free (e.g. Powderject™, Bioject™, etc.) injection.

Formulations for topical administration may be formulated to be immediate and/or modified release. Modified release formulations include delayed-, sustained-, pulsed-, controlled-, targeted and programmed release.

The compounds of the invention can also be administered intranasally or by inhalation, typically in the form of a dry powder (either alone, as a mixture, for example, in a dry blend with lactose, or as a mixed component particle, for example, mixed with phospholipids, such as phosphatidylcholine) from a dry powder inhaler, as an aerosol spray from a pressurised container, pump, spray, atomiser (preferably an atomiser using electrohydrodynamics to produce a fine mist), or nebuliser, with or without the use of a suitable propellant, such as 1,1,1,2-tetrafluoroethane or 1,1,1,2,3,3,3-heptafluoropropane, or as nasal drops. For intranasal use, the powder may comprise a bioadhesive agent, for example, chitosan or cyclodextrin.

The pressurised container, pump, spray, atomizer, or nebuliser contains a solution or suspension of the compound(s) of the invention comprising, for example, ethanol, aqueous ethanol, or a suitable alternative agent for dispersing, solubilising, or extending release of the active, a propellant(s) as solvent and an optional surfactant, such as sorbitan trioleate, oleic acid, or an oligolactic acid.

Prior to use in a dry powder or suspension formulation, the drug product is micronised to a size suitable for delivery by inhalation (typically less than 5 microns). This may be achieved by any appropriate comminuting method, such as spiral jet milling, fluid bed jet milling, supercritical fluid processing to form nanoparticles, high pressure homogenisation, or spray drying.

Capsules (made, for example, from gelatin or hydroxypropylmethylcellulose), blisters and cartridges for use in an inhaler or insufflator may be formulated to contain a powder mix of the compound of the invention, a suitable powder base such as lactose or starch and a performance modifier such as l-leucine, mannitol, or magnesium stearate. The lactose may be anhydrous or in the form of the monohydrate, preferably the latter. Other suitable excipients include dextran, glucose, maltose, sorbitol, xylitol, fructose, sucrose and trehalose.

A suitable solution formulation for use in an atomiser using electrohydrodynamics to produce a fine mist may contain from 1 μg to 20 mg of the compound of the invention per actuation and the actuation volume may vary from 1 μl to 100 μl. A typical formulation may comprise a compound of formula (I), propylene glycol, sterile water, ethanol and sodium chloride. Alternative solvents which may be used instead of propylene glycol include glycerol and polyethylene glycol.

Suitable flavours, such as menthol and levomenthol, or sweeteners, such as saccharin or saccharin sodium, may be added to those formulations of the invention intended for inhaled/intranasal administration.

Formulations for inhaled/intranasal administration may be formulated to be immediate and/or modified release using, for example, PGLA. Modified release formulations include delayed-, sustained-, pulsed-, controlled-, targeted and programmed release.

In the case of dry powder inhalers and aerosols, the dosage unit is determined by means of a valve which delivers a metered amount. Units in accordance with the invention are typically arranged to administer a metered dose or "puff". The overall daily dose may be administered in a single dose or, more usually, as divided doses throughout the day.

The compounds of the invention may be administered rectally or vaginally, for example, in the form of a suppository, pessary, or enema. Cocoa butter is a traditional suppository base, but various alternatives may be used as appropriate.

Formulations for rectal/vaginal administration may be formulated to be immediate and/or modified release. Modified release formulations include delayed-, sustained-, pulsed-, controlled-, targeted and programmed release.

The compounds of the invention may also be administered directly to the eye or ear, typically in the form of drops of a micronised suspension or solution in isotonic, pH-adjusted, sterile saline. Other formulations suitable for ocular and aural administration include ointments, gels, biodegradable (e.g. absorbable gel sponges, collagen) and non-biodegradable (e.g. silicone) implants, wafers, lenses and particulate or vesicular systems, such as niosomes or liposomes. A polymer such as crossed-linked polyacrylic acid, polyvinylalcohol, hyaluronic acid, a cellulosic polymer, for example, hydroxypropylmethylcellulose, hydroxyethylcellulose, or methyl cellulose, or a heteropolysaccharide polymer, for example, gelan gum, may be incorporated together with a preservative, such as benzalkonium chloride. Such formulations may also be delivered by iontophoresis.

Formulations for ocular/aural administration may be formulated to be immediate and/or modified release. Modified release formulations include delayed-, sustained-, pulsed-, controlled-, targeted, or programmed release.

The compounds of the invention may be combined with soluble macromolecular entities, such as cyclodextrin and suitable derivatives thereof or polyethylene glycol-containing polymers, in order to improve their solubility, dissolution rate, taste-masking, bioavailability and/or stability for use in any of the aforementioned modes of administration.

Drug-cyclodextrin complexes, for example, are found to be generally useful for most dosage forms and administration routes. Both inclusion and non-inclusion complexes may be used. As an alternative to direct complexation with the drug, the cyclodextrin may be used as an auxiliary additive, i.e. as a carrier, diluent, or solubiliser. Most commonly used for these purposes are alpha-, beta- and gamma-cyclodextrins, examples of which may be found in International Patent Applications Nos. WO 91/11172, WO 94/02518 and WO 98/55148.

For administration to human patients, the total daily dose of the compounds of the invention is typically in the range 0.1 mg to 1000 mg depending, of course, on the mode of administration. The total daily dose may be administered in single or divided doses and may, at the physician's discretion, fall outside of the typical range given herein.

These dosages are based on an average human subject having a weight of about 60 kg to 70 kg. The physician will readily be able to determine doses for subjects whose weight falls outside this range, such as infants and the elderly.

For the avoidance of doubt, references herein to "treatment" include references to curative, palliative and prophylactic treatment.

A $Na_{V1.8}$ channel modulator may be usefully combined with another pharmacologically active compound, or with two or more other pharmacologically active compounds, particularly in the treatment of pain. For example, a $Na_{V1.8}$ channel modulator, particularly a compound of formula (I), or a pharmaceutically acceptable salt or solvate thereof, as defined above, may be administered simultaneously, sequentially or separately in combination with one or more agents selected from:

an opioid analgesic, e.g. morphine, heroin, hydromorphone, oxymorphone, levorphanol, levallorphan, methadone, meperidine, fentanyl, cocaine, codeine, dihydrocodeine, oxycodone, hydrocodone, propoxyphene, nalmefene, nalorphine, naloxone, naltrexone, buprenorphine, butorphanol, nalbuphine or pentazocine;

a nonsteroidal antiinflammatory drug (NSAID), e.g. aspirin, diclofenac, diflusinal, etodolac, fenbufen, fenoprofen, flufenisal, flurbiprofen, ibuprofen, indomethacin, ketoprofen, ketorolac, meclofenamic acid, mefenamic acid, meloxicam, nabumetone, naproxen, nimesulide, nitroflurbiprofen, olsalazine, oxaprozin, phenylbutazone, piroxicam, sulfasalazine, sulindac, tolmetin or zomepirac;

a barbiturate sedative, e.g. amobarbital, aprobarbital, butabarbital, butabital, mephobarbital, metharbital, methohexital, pentobarbital, phenobartital, secobarbital, talbutal, theamylal or thiopental;

a benzodiazepine having a sedative action, e.g. chlordiazepoxide, clorazepate, diazepam, flurazepam, lorazepam, oxazepam, temazepam or triazolam;

an $H_1$ antagonist having a sedative action, e.g. diphenhydramine, pyrilamine, promethazine, chlorpheniramine or chlorcyclizine;

a sedative such as glutethimide, meprobamate, methaqualone or dichloralphenazone;

a skeletal muscle relaxant, e.g. baclofen, carisoprodol, chlorzoxazone, cyclobenzaprine, methocarbamol or orphrenadine;

an NMDA receptor antagonist, e.g. dextromethorphan ((+)-3-hydroxy-N-methylmorphinan) or its metabolite dextrorphan ((+)-3-hydroxy-N-methylmorphinan), ketamine, memantine, pyrroloquinoline quinine, cis-4-(phosphonomethyl)-2-piperidinecarboxylic acid, budipine, EN-3231 (MorphiDex®, a combination formulation of morphine and dextromethorphan), topiramate, neramexane or perzinfotel including an NR2B antagonist, e.g. ifenprodil, traxoprodil or (−)-(R)-6-{2-[4-(3-fluorophenyl)-4-hydroxy-1-piperidinyl]-1-hydroxyethyl-3,4-dihydro-2(1H)-quinolinone;

an alpha-adrenergic, e.g. doxazosin, tamsulosin, clonidine, guanfacine, dexmetatomidine, modafinil, or 4-amino-6,7-dimethoxy-2-(5-methane-sulfonamido-1,2,3,4-tetrahydroisoquinol-2-yl)-5-(2-pyridyl) quinazoline;

a tricyclic antidepressant, e.g. desipramine, imipramine, amitriptyline or nortriptyline;

an anticonvulsant, e.g. carbamazepine, lamotrigine, topiratmate or valproate;

a tachykinin (NK) antagonist, particularly an NK-3, NK-2 or NK-1 antagonist, e.g. (αR,9R)-7-[3,5-bis(trifluoromethyl)benzyl]-8,9,10,11-tetrahydro-9-methyl-5-(4-methylphenyl)-7H-[1,4]diazocino[2,1-g][1,7]-naphthyridine-6-13-dione (TAK-637), 5-[[(2R,3S)-2-[(1R)-1-[3,5-bis(trifluoromethyl)phenyl]ethoxy-3-(4-fluorophenyl)-4-morpholinyl]-methyl]-1,2-dihydro-3H-1,2,4-triazol-3-one (MK-869), aprepitant, lanepitant, dapitant or 3-[[2-methoxy-5-(trifluoromethoxy)phenyl]-methylamino]-2-phenylpiperidine (2S,3S);

a muscarinic antagonist, e.g oxybutynin, tolterodine, propiverine, tropsium chloride, darifenacin, solifenacin, temiverine and ipratropium;

a COX-2 selective inhibitor, e.g. celecoxib, rofecoxib, parecoxib, valdecoxib, deracoxib, etoricoxib, or lumiracoxib;

a coal-tar analgesic, in particular paracetamol;

a neuroleptic such as droperidol, chlorpromazine, haloperidol, perphenazine, thioridazine, mesoridazine, trifluoperazine, fluphenazine, clozapine, olanzapine, risperidone, ziprasidone, quetiapine, sertindole, aripiprazole, sonepiprazole, blonanserin, iloperidone, perospirone, raclopride, zotepine, bifeprunox, asenapine, lurasidone, amisulpride, balaperidone, palindore, eplivanserin, osanetant, rimonabant, meclinertant, Miraxion® or sarizotan;

a vanilloid receptor agonist (e.g. resinferatoxin) or antagonist (e.g. capsazepine);

a beta-adrenergic such as propranolol;

a local anaesthetic such as mexiletine;

a corticosteroid such as dexamethasone;

a 5-HT receptor agonist or antagonist, particularly a $5-HT_{1B/1D}$ agonist such as eletriptan, sumatriptan, naratriptan, zolmitriptan or rizatriptan;

a $5-HT_{2A}$ receptor antagonist such as R(+)-alpha-(2,3-dimethoxy-phenyl)-1-[2-(4-fluorophenylethyl)]-4-piperidinemethanol (MDL-100907);

a cholinergic (nicotinic) analgesic, such as ispronicline (TC-1734), (E)-N-methyl-4-(3-pyridinyl)-3-buten-1-amine (RJR-2403), (R)-5-(2-azetidinylmethoxy)-2-chloropyridine (ABT-594) or nicotine;

Tramadol®;

a PDEV inhibitor, such as 5-[2-ethoxy-5-(4-methyl-1-piperazinyl-sulphonyl)phenyl]-1-methyl-3-n-propyl-1,6-dihydro-7H-pyrazolo[4,3-d]pyrimidin-7-one (sildenafil), (6R,12aR)-2,3,6,7,12,12a-hexahydro-2-methyl-6-(3,4-methylenedioxyphenyl)-pyrazino[2',1':6,1]-pyrido[3,4-b]indole-1,4-dione (IC-351 or tadalafil), 2-[2-ethoxy-5-(4-ethyl-piperazin-1-yl-1-sulphonyl)-phenyl]-5-methyl-7-propyl-3H-imidazo[5,1-f][1,2,4]triazin-4-one (vardenafil), 5-(5-acetyl-2-butoxy-3-pyridinyl)-3-ethyl-2-(1-ethyl-3-azetidinyl)-2,6-dihydro-7H-pyrazolo[4,3-d]pyrimidin-7-one, 5-(5-acetyl-2-propoxy-3-pyridinyl)-3-ethyl-2-(1-isopropyl-3-azetidinyl)-2,6-dihydro-7H-pyrazolo[4,3-d]pyrimidin-7-one, 5-[2-ethoxy-5-(4-ethylpiperazin-1-ylsulphonyl)pyridin-3-yl]-3-ethyl-2-[2-methoxyethyl]-2,6-dihydro-7H-pyrazolo[4,3-d]pyrimidin-7-one, 4-[(3-chloro-4-methoxybenzyl)amino]-2-[(2S)-2-(hydroxymethyl)pyrrolidin-1-yl]-N-(pyrimidin-2-ylmethyl)pyrimidine-5-carboxamide, 3-(1-methyl-7-oxo-3-propyl-6,7-dihydro-1H-pyrazolo[4,3-d]pyrimidin-5-yl)-N-[2-(1-methylpyrrolidin-2-yl)ethyl]-4-propoxybenzenesulfonamide;

an alpha-2-delta ligand such as gabapentin, pregabalin, 3-methylgabapentin, (1α,3α,5α)(3-amino-methyl-bicyclo[3.2.0]hept-3-yl)-acetic acid, (3S,5R)-3-aminomethyl-5-methyl-heptanoic acid, (3S,5R)-3-amino-5-methyl-heptanoic acid, (3S,5R)-3-amino-5-methyl-octanoic acid, (2S,4S)-4-(3-chlorophenoxy)proline, (2S,4S)-4-(3-fluorobenzyl)-proline, [(1R,5R,6S)-6-(aminomethyl)bicyclo[3.2.0]hept-6-yl]acetic acid, 3-(1-aminomethyl-cyclohexylmethyl)-4H-[1,2,4]oxadiazol-5-one, C-[1-(1H-tetrazol-5-ylmethyl)-cycloheptyl]-methylamine, (3S,4S)-(1-aminomethyl-3,4-dimethyl-cyclopentyl)-acetic acid, (3S,5R)-3-aminomethyl-5-methyl-octanoic acid, (3S,5R)-3-amino-5-methyl-nonanoic acid, (3S,5R)-3-amino-5-methyl-octanoic acid, (3R,4R,5R)-3-amino-4,5-dimethyl-heptanoic acid and (3R,4R,5R)-3-amino-4,5-dimethyl-octanoic acid;

a cannabinoid;

metabotropic glutamate subtype 1 receptor (mGluR1) antagonist;

a serotonin reuptake inhibitor such as sertraline, sertraline metabolite demethylsertraline, fluoxetine, norfluoxetine (fluoxetine desmethyl metabolite), fluvoxamine, paroxetine, citalopram, citalopram metabolite desmethylcitalopram, escitalopram, d,l-fenfluramine, femoxetine, ifoxetine, cyanodothiepin, litoxetine, dapoxetine, nefazodone, cericlamine and trazodone;

a noradrenaline (norepinephrine) reuptake inhibitor, such as maprotiline, lofepramine, mirtazepine, oxaprotiline, fezolamine, tomoxetine, mianserin, buprorion, buprorion metabolite hydroxybuprorion, nomifensine and viloxazine (Vivalan®), especially a selective noradrenaline reuptake inhibitor such as reboxetine, in particular (S,S)-reboxetine;

a dual serotonin-noradrenaline reuptake inhibitor, such as venlafaxine, venlafaxine metabolite O -desmethylvenlafaxine, clomipramine, clomipramine metabolite desmethylclomipramine, duloxetine, milnacipran and imipramine;

an inducible nitric oxide synthase (iNOS) inhibitor such as S-[2-[(1-iminoethyl)amino]ethyl]-L-homocysteine, S-[2-[(1-iminoethyl)-amino]ethyl]-4,4-dioxo-L-cysteine, S-[2-[(1-iminoethyl)amino]ethyl]-2-methyl-L-cysteine, (2S,5Z)-2-amino-2-methyl-7-[(1-iminoethyl) amino]-5-heptenoic acid, 2-[[(1R,3S)-3-amino-4-hydroxy-1-(5-thiazolyl)-butyl]thio]-5-chloro-3-pyridinecarbonitrile; 2-[[(1R,3S)-3-amino-4-hydroxy- 1-(5-thiazolyl)butyl]thio]-4-chlorobenzonitrile, (2S,4R)-2-amino-4-[[2-chloro-5-(trifluoromethyl)phenyl]thio]-5-thiazolebutanol, 2-[[(1R,3S)-3-amino-4-hydroxy-1-(5-thiazolyl)butyl]thio]-6-(trifluoromethyl)-3 pyridinecarbonitrile, 2-[[(1R,3S)-3-amino-4-hydroxy-1-(5-thiazolyl)butyl]thio]-5-chlorobenzonitrile, N-[4-[2-(3-chlorobenzylamino)ethyl]phenyl]thiophene-2-carboxamidine, or guanidinoethyldisulfide;

an acetylcholinesterase inhibitor such as donepezil;

a prostaglandin $E_2$ subtype 4 (EP4) antagonist such as N-[({2-[4-(2-ethyl-4,6-dimethyl-1H-imidazo[4,5-c]pyridin-1-yl)phenyl]ethyl}amino)-carbonyl]-4-methyl-benzenesulfonamide or 4-[(1S)-1-({[5-chloro-2-(3-fluorophenoxy)pyridin-3-yl]carbonyl}amino)ethyl] benzoic acid;

a leukotriene B4 antagonist; such as 1-(3-biphenyl-4-ylmethyl-4-hydroxy-chroman-7-yl)-cyclopentanecarboxylic acid (CP-105696), 5-[2-(2-Carboxyethyl)-3-[6-(4-methoxyphenyl)-5E-hexenyl]oxyphenoxy]-valeric acid (ONO-4057) or DPC-11870, a 5-lipoxygenase inhibitor, such as zileuton, 6-[(3-fluoro-5-[4-methoxy-3,4,5,6-tetrahydro-2H-pyran-4-yl])phenoxy-methyl]-1-methyl-2-quinolone (ZD-2138), or 2,3,5-trimethyl-6-(3-pyridylmethyl), 1,4-benzoquinone (CV-6504);

a sodium channel blocker, such as lidocaine;

a 5-HT3 antagonist, such as ondansetron;

and the pharmaceutically acceptable salts and solvates thereof.

Such combinations offer significant advantages, including synergistic activity, in therapy.

Inasmuch as it may desirable to administer a combination of active compounds, for example, for the purpose of treating a particular disease or condition, it is within the scope of the present invention that two or more pharmaceutical compositions, at least one of which contains a compound in accordance with the invention, may conveniently be combined in the form of a kit suitable for coadministration of the compositions.

Thus the kit of the invention comprises two or more separate pharmaceutical compositions, at least one of which contains a compound of formula (I) in accordance with the invention, and means for separately retaining said compositions, such as a container, divided bottle, or divided foil packet. An example of such a kit is the familiar blister pack used for the packaging of tablets, capsules and the like.

The kit of the invention is particularly suitable for administering different dosage forms, for example, oral and parenteral, for administering the separate compositions at different dosage intervals, or for titrating the separate compositions against one another. To assist compliance, the kit typically comprises directions for administration and may be provided with a so-called memory aid.

All of the pyrazine derivatives of the formula (I) can be prepared by the procedures described in the general methods presented below or by routine modifications thereof. The present invention also encompasses any one or more of these processes for preparing the pyrazine derivatives of formula (I), in addition to any novel intermediates used therein.

In the following general methods, Ar and $R^1$ are as previously defined for a pyrazine derivative of the formula (I) unless otherwise stated. Where ratios of solvents are given, the ratios are by volume.

According to a first process, compounds of formula (I) may be prepared from compounds of formula (V), as illustrated by Scheme 1.

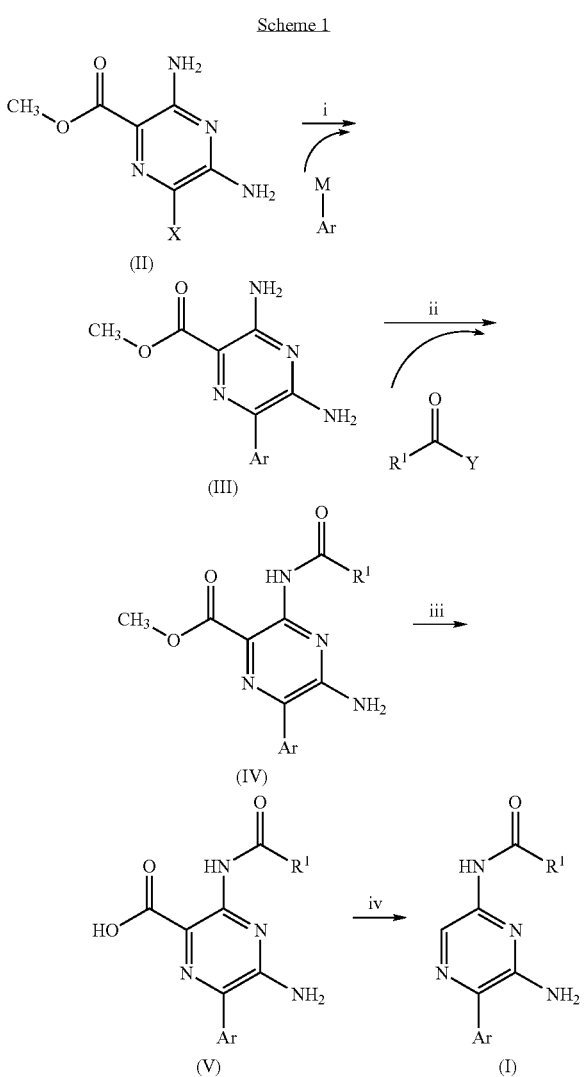

M is an optionally substituted metal or boron group suitable for cross-coupling reactions such as a trialkylstannane, dihydroxyborane, dialkoxyborane or halozinc.

X is a suitable group for cross-coupling reactions, typically Cl, Br or I

Y is a suitable leaving group, typically Cl

Compounds of formula (II) are either commercially available, in the case of the chloro derivative, or are known in the literature (J. Med. Chem. 1967, 10(1), 66-75).

Compounds of formula (III) can be prepared from compounds of formula (II) by process step (i), a cross-coupling reaction, with ArM, in the presence of a suitable catalyst system, (e.g. palladium or nickel), and base. Typically 'Suzuki' conditions are used, comprising 1.2-3 equivalents of boronic acid, base and 0.01-0.25 equivalents of a palladium catalyst with phosphine based ligands in an organic solvent at a temperature of from 50° C. to 100° C. Preferred conditions comprise 2 equivalents of boronic acid, 1 equivalent of Cs$_2$CO$_3$ and 0.1 equivalents Pd(PPh$_3$)$_4$ in 2:1 1,4-dioxane/water at 80° C.

Compounds of formula (IV) can be prepared from compounds of formula (III) according to process step (ii), an amide coupling using an acid chloride or a carboxylic acid activated by a suitable agent, optionally in the presence of a catalyst, in a suitable solvent. Typical conditions comprise acid chloride and an amine of formula (III), with an excess of a suitable organic base, such as Et$_3$N, lutidine or pyridine, in a suitable solvent, at a temperature of from room temperature to 80° C. Preferred conditions comprise 1.5 equivalents acid chloride in pyridine at 60° C., or with 1.5 equivalents lutidine in acetonitrile at room temperature.

Compounds of formula (V) can be prepared from compounds of formula (IV) according to process step (iii), an ester hydrolysis reaction under basic, or acidic conditions. Typical conditions are base mediated, using an alkali metal base such as LiOH, NaOH, KOH or K$_2$CO$_3$ in the presence of water and a suitable solvent at a temperature of from room temperature to 100° C. Preferred conditions comprise 3 equivalents of LiOH.H$_2$O in 3:1 CH$_3$OH/H$_2$O at 75° C.

Compounds of formula (I) can be prepared from compounds of formula (V) by decarboxylation under basic or acidic conditions requiring a temperature of from 50° C. to 150° C. (process step (iv)). Typical conditions comprise an excess of aqueous acid in a suitable organic solvent at a temperature of from 50° C. to 100° C. Preferably the decarboxylation step is carried at reflux in 2:1 1N aqueous HCl/1,4-dioxane.

According to a second process, compounds of formula (I) may be prepared from compounds of formula (VII), as illustrated by Scheme 2.

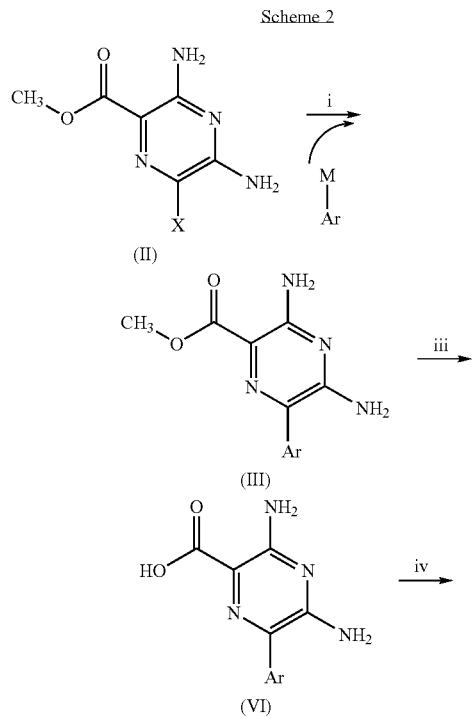

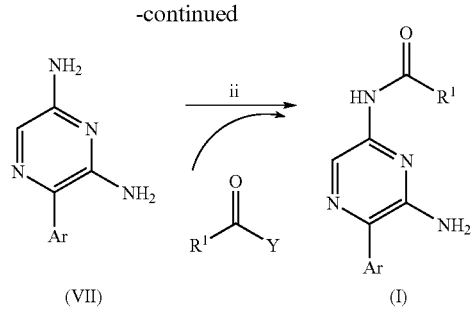

wherein M, X and Y are as defined for Scheme 1.

Compounds of formula (III) can be prepared from compounds of formula (II) according to process step (i) as described above for Scheme 1.

Compounds of formula (VI) can be prepared from compounds of formula (III) by ester hydrolysis according to process step (iii) as described above for Scheme 1.

Compounds of formula (VII) can be prepared from compounds of formula (VI) by decarboxylation according to process step (iv) as described above for Scheme 1.

Compounds of formula (I) can be prepared from compounds of formula (VIII) by an amide coupling reaction according to process step (ii) as described above for Scheme 1.

Compounds of formula (VII) may also be prepared according to a third process as described in WO-A-98/3817 (Scheme 3).

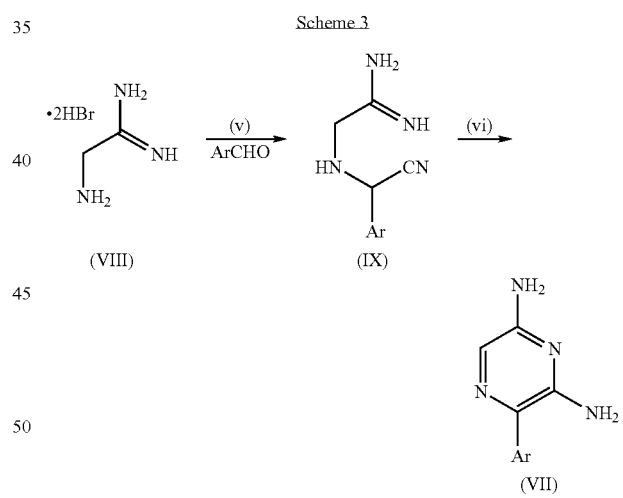

Compounds of formula (IX) may be prepared, according to process step (v), by reacting compounds of formula (VIII) or a salt thereof, for example aminoacetamidine, with compounds of formula ArCHO in the presence of a cyanide source, for example potassium cyanide.

Compounds of formula (VII) may be prepared by cyclisation and oxidation of a compound of formula (IX) in the presence of lithium hydroxide in a suitable alcoholic solvent such as methanol, with the reaction open to the air for oxidation.

According to a fourth process, compounds of formula (I) may be prepared from compounds of formula (XII), as illustrated by Scheme 4.

Scheme 4

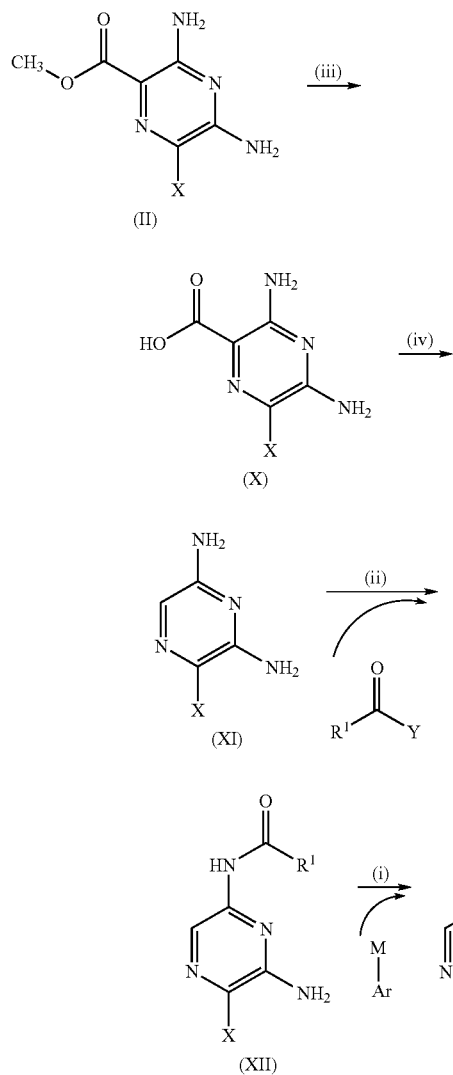

M, X and Y are as defined for Scheme 1.

Compounds of formula (X) can be prepared from compounds of formula (II) by ester hydrolysis according to process step (iii) as described above for Scheme 1.

Compounds of formula (XI) can be prepared from compounds of formula (X) by decarboxylation according to process step (iv) as described above for Scheme 1.

Compounds of formula (XII) can be prepared from compounds of formula (XI) by an amide coupling reaction according to process step (ii) as described above for Scheme 1.

Compounds of formula (I) can be prepared from compounds of formula (XII) by a cross-coupling reaction according to process step (i) as described above for Scheme 1.

Compounds of formula (XI) may alternatively be prepared from compounds of formula (XIII), as illustrated by Scheme 5.

Scheme 5

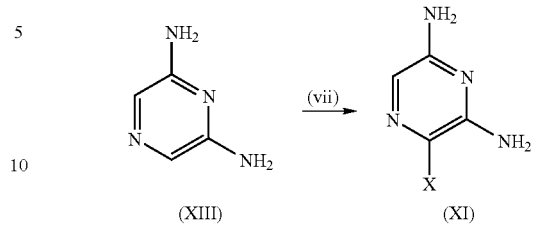

wherein X is a halogen atom.

2,6-Diaminopyrazine may be prepared as described in J. Chem. Soc. Perkin Trans. 1: Organic and Bio-Organic Chemistry (1972-1999) 1973, 6, 606.

Compounds of formula (XI) may be prepared by an electrophilic halogenation reaction according to reaction step (vii). Typical conditions comprise reaction of 2,6-diaminopyrazine with a halogen, optionally in the presence of a catalyst, e.g. iodine and silver acetate or bromine in a suitable solvent. Preferred conditions comprise bromine in acetic acid at room temperature.

Alternatively, compounds of formula (XII) may be prepared from compounds of formula (XIV), as illustrated by Scheme 6.

Scheme 6

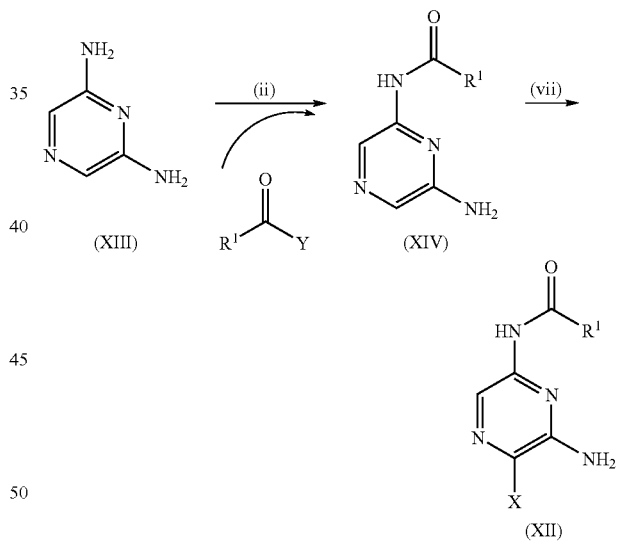

wherein Y is as defined for Scheme 1; and

X is a halogen atom.

Compounds of formula (XIV) may be prepared from compounds of formula (XIII) by an amide coupling reaction according to process step (ii) as described for Scheme 1.

Compounds of formula (XII) may be prepared from compounds of formula (XIV) by an electrophilic halogenation reaction according to process step (vii) as described for Scheme 5.

Referring to the general methods above, it will be readily understood to the skilled person that where protecting groups are present, these will be generally interchangeable with other protecting groups of a similar nature, e.g. where an amine is described as being protected with a tert-butoxycarbonyl group, this may be readily interchanged with any suitable amine protecting group. Suitable protecting groups are described in 'Protective Groups in Organic Synthesis' by T. Greene and P. Wuts (3$^{rd}$ edition, 1999, John Wiley and Sons).

The present invention also relates to novel intermediate compounds as defined above, all salts, solvates and complexes thereof and all solvates and complexes of salts thereof as defined hereinbefore for pyrazine derivatives of formula (I). The invention includes all polymorphs of the aforementioned species and crystal habits thereof.

When preparing pyrazine derivatives of formula (I) in accordance with the invention, it is open to a person skilled in the art to routinely select the form of the intermediate compounds which provides the best combination of features for this purpose. Such features include the melting point, solubility, processability and yield of the intermediate form and the resulting ease with which the product may be purified on isolation.

The invention is illustrated by the following representative Examples.

$^1$H Nuclear magnetic resonance (NMR) spectra were in all cases consistent with the proposed structures. Characteristic chemical shifts (δ) are given in parts-per-million downfield from tetramethylsilane using conventional abbreviations for designation of major peaks: e.g. s, singlet; d, doublet; t, triplet; q, quartet; m, multiplet; br, broad. The mass spectra (MS) were recorded using either electrospray ionisation (ESI) or atmospheric pressure chemical ionisation (APCI). The following abbreviations have been used for common solvents: CDCl$_3$, deuterochloroform; D$_6$-DMSO, deuterodimethylsulphoxide; CD$_3$OD, deuteromethanol; THF, tetrahydrofuran. LCMS indicates liquid chromatography mass spectrometry ($R_f$=retention time). Where ratios of solvents are given, the ratios are by volume.

Certain compounds of the Examples and Preparations were purified using Automated Preparative High Performance Liquid Chromatography (HPLC). Reversed-phase HPLC conditions were on FractionLynx systems. Samples were submitted dissolved in 1 mL of DMSO. Depending on the nature of the compounds and the results of a pre-analysis, the purification was performed under either acidic conditions or basic conditions at ambient temperature. Acidic runs were carried out on a Sunfire Prep C18 OBD column (19×50 mm, 5 μm), basic runs were carried out on a Xterra Prep MS C18 (19×50 mm, 5 μm), both from Waters. A flow rate of 18 mL/min was used with mobile phase A: water+0.1% modifier (v/v) and B: acetonitrile+0.1% modifier (v/v). For acidic runs the modifier was formic acid, for basic run the modifier was diethylamine. A Waters 2525 binary LC pump supplied a mobile phase with a composition of 5% B for 1 min then ran from 5% to 98% B over 6 min followed by a 2 min hold at 98% B. Detection was achieved using a Waters 2487 dual wavelength absorbance detector set at 225 nm followed in series by a Polymer Labs PL-ELS 2100 detector and a Waters ZQ 2000 4 way MUX mass spectrometer in parallel. The PL 2100 ELSD was set at 30° C. with 1.6 L/min supply of Nitrogen. The Waters ZQ MS was tuned with the following parameters:

ES+ Cone voltage: 30 v Capillary: 3.20 kv

ES− Cone voltage: −30 v Capillary: −3.00 kv

Desolvation gas: 600 L/hr

Source Temp: 120° C.

Scan range 150-900 Da

The fraction collection was triggered by both MS and ELSD.

Quality control analysis was performed using a LCMS method orthogonal to the preparative method. Acidic runs were carried out on a Sunfire C18 (4.6×50 mm, 5 μm), basic runs were carried out on a Xterra C18 (4.6×50 mm, 5 μm), both from Waters. A flow rate of 1.5 mL/min was used with mobile phase A: water+0.1% modifier (v/v) and B: acetonitrile+0.1% modifier (v/v). For acidic runs the modifier was formic acid, for basic run the modifier was diethylamine. A Waters 1525 binary LC pump ran a gradient elution from 5% to 95% B over 3 min followed by a 1 min hold at 95% B. Detection was achieved using a Waters MUX UV 2488 detector set at 225 nm followed in series by a Polymer Labs PL-ELS 2100 detector and a Waters ZQ 2000 4 way MUX mass spectrometer in parallel. The PL 2100 ELSD was set at 30° C. with 1.6 L/min supply of Nitrogen. The Waters ZQ MS was tuned with the following parameters:

ES+ Cone voltage: 25 v Capillary: 3.30 kv

ES− Cone voltage: −30 v Capillary: −2.50 kv

Desolvation gas: 800 L/hr

Source Temp: 150° C.

Scan range 160-900 Da

EXAMPLE 1

N-[6-Amino-5-(2,3,5-trichlorophenyl)pyrazin-2-yl]-1-methyl-1H-pyrazole-5-carboxamide (also known as 2-methyl-2H-pyrazole-3-carboxylic acid [6-amino-5-(2,3,5-trichlorophenyl)-pyrazin-2-yl]-amide)

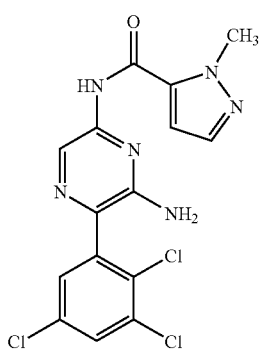

Method A

N-(6-Amino-5-chloropyrazin-2-yl)-1-methyl-1H-pyrazole-5-carboxamide (Preparation 2, 0.05 g, 0.198 mmol) was combined with 2,3,5-trichlorobenzeneboronic acid (0.062 g, 0.28 mmol), cesium carbonate (0.045 g, 0.14 mmol) and palladium tetrakistriphenylphosphine (0.016 g, 0.014 mmol) and suspended in a mixture of 1,4-dioxane (5 ml) and water (1 ml). The reaction was heated at 75° C. for 5 hours and further aliquots of cesium carbonate (0.04 g) and palladium tetrakistriphenylphosphine (0.01 g) were added. After a further 1 hour at 75° C. the reaction was allowed to cool to room temperature and then concentrated in vacuo. The residue was partitioned between water and ethyl acetate and the organic layer dried (MgSO$_4$) and evaporated. The residue was purified by silica gel column chromatography, eluting with ethyl acetate:heptane 1:1, to afford the product as an off-white solid (30 mg).

¹HNMR (d$_6$-DMSO): 4.09 (s, 3H), 6.13 (br s, 2H), 7.25 (d, 1H), 7.50-7.51 (m, 2H), 7.90 (d, 1H), 8.55 (s, 1H), 10.60 (br s, 1H).

MS m/z 397 [MH]⁺

EXAMPLE 2

N-[6-Amino-5-(2-chloro-5-methoxyphenyl)pyrazin-2-yl]-1-methyl-1H-pyrazole-5-carboxamide

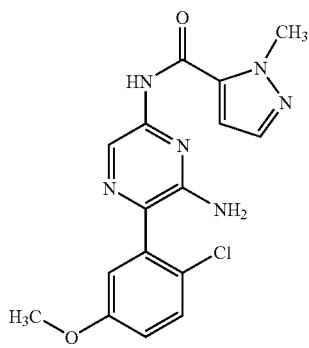

Method B

Oxalyl chloride (11.3 g, 89.5 mmol) was added to a slurry of 1-methyl-1H-pyrazole-5-carboxylic acid (7.5 g, 59.5 mmol) in dichloromethane (100 ml). One drop dimethylformamide was added and the reaction left to stir at room temperature for 7 hours. Another 7 ml oxalyl chloride was added followed by 1 drop dimethylformamide, and the reaction left to stir at room temperature overnight. The reaction was concentrated in vacuo and azeotroped with dichloromethane. The residue was dissolved in CH$_3$CN (20 ml) and added to a solution of the 3-(2-chloro-5-methoxy-phenyl)-pyrazine-2,6-diamine (Preparation 6, 9.0 g, 35.9 mmol) and lutidine (5.2 ml, 46.7 mmol) in CH$_3$CN (100 ml). The reaction was stirred at room temperature for 4 hours before concentration in vacuo. The residue was taken up in 200 ml ethyl acetate and washed with 100 ml water. The organic layer was collected and washed again with 50 ml water and 50 ml brine, before drying over MgSO$_4$ and concentrating in vacuo to afford a sticky gum. The residue was purified by silica gel column chromatography, eluting with ethyl acetate:heptane 2:1, to afford the product as a white solid.

¹HNMR (d$_6$-DMSO): 3.8 (3H, s), 4.1 (3H, s), 5.85 (2H, br s), 6.95 (1H, m), 7.05 (1H, m), 7.25 (1H, m), 7.45 (1H, m), 7.5 (1H, m), 8.55 (1H, s).

LCMS Rt=3.35 min

MS m/z 359 [MH]+

EXAMPLE 3

N-[6-Amino-5-(7-chloro-2,3-dihydro-1,4-benzo-dioxin-5-yl)pyrazin-2-yl]-1-methyl-1H-pyrazole-5-carboxamide

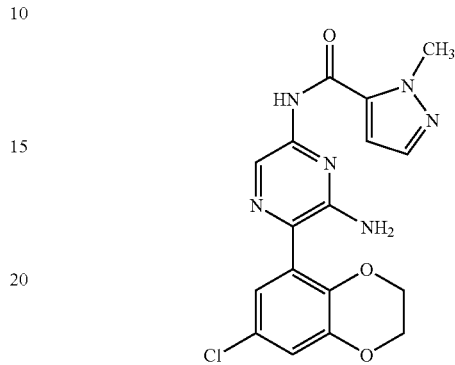

Method C

Oxalyl chloride (36 μl, 0.41 mmol) was added to a slurry of 1-methyl-1H-pyrazole-5-carboxylic acid (40 mg, 0.32 mmol) in dichloromethane (2 ml). One drop dimethylformamide was added and the reaction left to stir at room temperature for 3 hours before concentrating in vacuo and azeotroping with dichloromethane. The resulting acid chloride was dissolved in 1 ml anhydrous pyridine and added to a solution of 3-(7-chloro-2,3-dihydro-benzo[1,4]dioxin-5-yl)-pyrazine-2,6-diamine (Preparation 13, 50 mg, 0.18 mmol) in 2 ml anhydrous pyridine. The reaction was heated to 60° C. overnight before concentrating in vacuo and partitioning between 5 ml dichloromethane and 5 ml water. The layers were separated using a phase separation cartridge and the organic layer collected and concentrated in vacuo. The residue was dissolved in 1 ml dimethylsulfoxide and purified using preparative HPLC.

LCMS Rt=3.14 min

MS m/z 388 [MH]+

The following examples of the general formula:

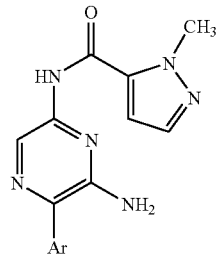

were prepared by methods analogous to Methods A and B, as described for Examples 1 and 2 above. Unless otherwise noted, preparation details are as described for the method referred to.

| Example No. | Ar | Name | Data | Preparation information |
|---|---|---|---|---|
| 4 | 2-chloro-5-fluorophenyl | N-[6-amino-5-(2-chloro-5-fluorophenyl)pyrazin-2-yl]-1-methyl-1H-pyrazole-5-carboxamide | LCMS Rt=2.92min<br>MS m/z 347[MH]+ | Method A, using N-(6-amino-5-chloropyrazin-2-yl)-1-methyl-1H-pyrazole-5-carboxamide (Preparation 2) and 2-chloro-5-fluorophenylboronic acid. |
| 5 | 2,3-dichlorophenyl | N-[6-amino-5-(2,3-dichlorophenyl)pyrazin-2-yl]-1-methyl-1H-pyrazole-5-carboxamide | MS m/z 363[MH]+<br>$^1$HNMR(CDCl$_3$): 4.25(s, 3H), 4.45(br, s, 2H), 6.72(s, 1H), 7.35(m, 2H), 7.53(s, 1H), 7.57(m, 1H), 8.04(br s, 1H), 9.02(s, 1H). | Method A, using N-(6-amino-5-chloropyrazin-2-yl)-1-methyl-1H-pyrazole-5-carboxamide (Preparation 2) and 1.5 equivalents of 2,3-dichlorophenylboronic acid, 1 equivalent cesium carbonate and 0.1 equivalents palladium tetrakis(triphenylphosphine). |
| 6 | 2,5-dichloro-3-methoxyphenyl | N-[6-amino-5-(2,5-dichloro-3-methoxyphenyl)pyrazin-2-yl]-1-methyl-1H-pyrazole-5-carboxamide | MS m/z 393[MH]+<br>$^1$HNMR(CDCl$_3$): 3.93(s, 3H), 4.22(s, 3H), 4.43(br, s, 2H), 6.70(s, 1H), 7.00(s, 1H), 7.04(s, 1H), 7.50(s, 1H), 7.98(br s, 1H), 8.97(s, 1H). | Method A, using N-(6-amino-5-chloropyrazin-2-yl)-1-methyl-1H-pyrazole-5-carboxamide (Preparation 2), 2-(2,5-dichloro-3-methoxy-phenyl)-4,4,5,5-tetramethyl-[1,3,2]dioxaborolane (Preparation 20). 1 equivalent cesium carbonate and 0.1 equivalents palladium tetrakis(triphenylphosphine). |
| 7 | 2,5-dichlorophenyl | N-[6-amino-5-(2,5-dichlorophenyl)pyrazin-2-yl]-1-methyl-1H-pyrazole-5-carboxamide (also known as 2-methyl-2H-pyrazole-3-carboxylic acid [6-amino-5-(2,5-dichlorophenyl)-pyrazin-2-yl]-amide) | MS m/z 363[MH]$^+$<br>$^1$HNMR(d$_6$-DMSO): 4.10(s, 3H), 6.00(br s, 2H), 7.15(s, 1H), 7.50-7.60(m, 4H), 8.60(s, 1H), 10.60(br s, 1H). | Method A, using N-(6-amino-5-chloropyrazin-2-yl)-1-methyl-1H-pyrazole-5-carboxamide (Preparation 2) and 2,5-dichlorophenylboronic acid. |
| 8 | 2-chloro-3-methoxyphenyl | N-[6-amino-5-(2-chloro-3-methoxyphenyl)pyrazin-2-yl]-1-methyl-1H-pyrazole-5-carboxamide | MS m/z 359[MH]+<br>$^1$HNMR(CDCl$_3$): 3.97(s, 3H), 4.26(s, 3H), 4.47(br s, 2H), 6.71(s, 1H), 7.03(d, 2H), 7.37(t, 1H), 7.53(s, 1H), 7.99(br s, 1H), 9.01(s, 1H) | Method B, using 3-(2-chloro-3-methoxyphenyl)pyrazine-2,6-diamine (Preparation 15), 1.15 equivalents lutidine and 1.1 equivalents acid chloride prepared from 1-methyl-1H-pyrazole-5-carboxylic acid. |
| 9 | 2,3-dichloro-6-methoxyphenyl | N-[6-amino-5-(2,3-dichloro-6-methoxyphenyl)pyrazin-2-yl]-1-methyl-1H-pyrazole-5-carboxamide | MS m/z 394[MH]+<br>$^1$HNMR(CDCl$_3$): 3.76(s, 3H), 4.25(s, 3H), 4.35(br s, 2H), 6.71(s, 1H), 6.90(d, 1H), 7.52(d, 1H), 8.01(br s, 1H), 9.05(s, 1H). | Method B, using 3-(2,3-dichloro-6-methoxyphenyl)pyrazine-2,6-diamine (Preparation 14), 1.2 equivalents lutidine and 1.1 equivalents acid chloride prepared from 1-methyl-1H-pyrazole-5-carboxylic acid,. |
| 10 | 2-chloro-5-(trifluoromethyl)phenyl | N-{6-amino-5-[2-chloro-5-(trifluoromethyl)phenyl]pyrazin-2-yl}-1-methyl-1H-pyrazole-5-carboxamide | LCMS Rt=2.67min<br>MS m/z 397[MH]+ | Method A, using N-(6-amino-5-chloropyrazin-2-yl)-1-methyl-1H-pyrazole-5-carboxamide (Preparation 2) and 2-chloro-5-(trifluoromethyl)benzeneboronic acid. Heated at 80° C. for 3 hours. |
| 11 | 2-chloro-5-cyanophenyl | N-[6-amino-5-(2-chloro-5-cyanophenyl)pyrazin-2-yl]-1-methyl-1H-pyrazole-5-carboxamide | LCMS Rt=2.31min<br>MS ES+ 354 ES− 352 | Method A, using N-(6-amino-5-chloropyrazin-2-yl)-1-methyl-1H-pyrazole-5-carboxamide (Preparation 2) and 2-chloro-5-cyanophenylboronic acid. Heated at 80° C. for 3 hours. |

EXAMPLE 12

N-[6-Amino-5-(2,3-dichloro-5-methoxyphenyl)pyrazin-2-yl]-1-methyl-1H-pyrazole-5-carboxamide

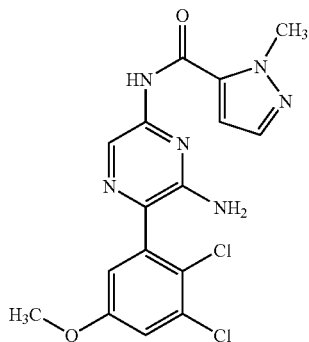

N-(6-Amino-5-chloropyrazin-2-yl)-1-methyl-1H-pyrazole-5-carboxamide (Preparation 2, 0.1 g, 0.396 mmol) was combined with 2,(2,3-dichloro-5-methoxy-phenyl-4,4,5,5-tetramethyl-[1,3,2]dioxaborolane (Preparation 18), (0.156 g, 0.515 mmol), cesium carbonate (0.129 g, 0.396 mmol) and palladium tetrakistriphenylphosphine (0.046 g, 0.04 mmol) and suspended in a mixture of 1,4-dioxane (1 ml) and water (0.5 ml). The reaction was heated at 80° C. for 5 hours. The reaction was allowed to cool to room temperature and then concentrated in vacuo. The residue was partitioned between aqueous sodium carbonate solution (20 ml) and ethyl acetate (20 ml) and the organic layer dried (Na$_2$SO$_4$) and concentrated in vacuo. The residue was purified by silica gel column chromatography, eluting with ethyl acetate:heptane 2:3 to 1:1, to afford the product as an off-white solid (72 mg).

MS m/z 393 [MH]+

$^1$HNMR (CDCl$_3$): 3.80 (s, 3H), 4.23 (s, 3H), 4.43 (br, s, 2H), 6.70 (s, 1H), 6.90 (d, 1H), 7.10 (s, 1H), 7.50 (d, 1H), 8.05 (br s, 1H), 9.05 (s, 1H).

The following examples of the general formula:

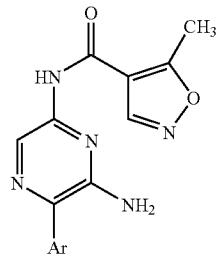

were prepared by methods analogous to Methods A and B, as described above for Examples 1 and 2. Unless otherwise noted, preparation details are as described for the method referred to.

| Example No. | Ar | Name | Data | Preparation information |
|---|---|---|---|---|
| 13 | 2,5-dichloro-3-methoxyphenyl | N-[6-amino-5-(2,5-dichloro-3-methoxyphenyl)pyrazin-2-yl]-5-methylisoxazole-4-carboxamide | LCMS Rt=1.62min MS m/z 393[MH]+ | Method B, using 3-(2,5-dichloro-3-methoxyphenyl)pyrazine-2,6-diamine (Preparation 9), 1.5 equivalents lutidine and 1.5 equivalent of acid chloride, prepared from 5-methyl-isoxazole-4-carboxylic acid. Stirred for 18 hours. |
| 14 | 2,3,5-trichlorophenyl | N-[6-amino-5-(2,3,5-trichlorophenyl)pyrazin-2-yl]-5-methylisoxazole-4-carboxamide (also known as 5-methyl-isoxazole-4-carboxylic acid [6-amino-5-(2,3,5-trichlorophenyl)-pyrazin-2-yl]-amide) | MS m/z 398[MH]$^+$ $^1$HNMR(d$_6$-DMSO): 2.68(s, 3H), 6.11(br s, 2H), 7.50(d, 1H), 7.89(d, 1H), 8.58(s, 1H), 9.19(s, 1H), 10.60(br s, 1H). | Method A, using N-(6-amino-5-chloropyrazin-2-yl)-5-methylisoxazole-4-carboxamide (Preparation 4) and 2,3,5-trichlorophenylboronic acid. |
| 15 | 2-chloro-5-methoxyphenyl | N-[6-amino-5-(2-chloro-5-methoxyphenyl)pyrazin-2-yl]-5-methylisoxazole-4-carboxamide | LCMS Rt=2.30min MS m/z 360[MH]+ | Method B, using 5-methyl-isoxazole-4-carboxylic acid and 3-(2-chloro-5-methoxy-phenyl)-pyrazine-2,6-diamine (Preparation 6). |

The following examples of the general formula:

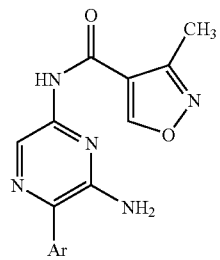

were prepared by methods analogous to Methods A and C, as described above for Examples 1 and 3. Unless otherwise noted, preparation details are as described for the method referred to.

| Example No. | Ar | Name | Data | Preparation information |
|---|---|---|---|---|
| 16 | 2-chlorophenyl | N-[6-amino-5-(2-chlorophenyl)pyrazin-2-yl]-3-methylisoxazole-4-carboxamide | MS m/z 330[MH]+ $^1$HNMR(CDCl$_3$): 2.6(s, 3H), 4.5(br s, 2H), 7.4(m, 3H), 7.5(m, 1H), 7.9(br s, 1H), 8.85(s, 1H), 9.0(s, 1H). | Method A, using N-(6-amino-5-chloropyrazin-2-yl)-3-methylisoxazole-4-carboxamide (Preparation 3), 1.1 equivalents 2-chlorophenylboronic acid, 1.2 equivalents cesium carbonate, and 0.05 equivalents Pd(PPh$_3$)$_4$. Heated for 1 hour at 80° C. |
| 17 | 2,3-dichlorophenyl | N-[6-amino-5-(2,3-dichlorophenyl)pyrazin-2-yl]-3-methylisoxazole-4-carboxamide | MS m/z 364[MH]+ $^1$HNMR(CDCl$_3$): 2.6(s, 3H), 4.5(br s, 2H), 7.35(d, 2H), 7.6(m, 1H), 8.0(br s, 1H), 8.9(s, 1H), 9.0(s, 1H). | Method A, using N-(6-amino-5-chloropyrazin-2-yl)-3-methylisoxazole-4-carboxamide (Preparation 3), 1.1 equivalents 2,3-dichlorophenylboronic acid, 1.5 equivalents cesium carbonate, 0.2 equivalents Pd(PPh$_3$)$_4$. Heated for 1 hour at 80° C. |
| 18 | 2,3,5-trichlorophenyl | N-[6-amino-5-(2,3,5-trichlorophenyl)pyrazin-2-yl]-methylisoxazole-4-carboxamide (also known as 3-methyl-isoxazole-4-carboxylic acid [6-amino-5-(2,3,5-trichlorophenyl)-pyrazin-2-yl]-amide) | MS m/z 398[MH]$^+$ $^1$HNMR(d$_6$-DMSO): 2.42(s, 3H), 6.15(br s, 2H), 7.50(d, 1H), 7.91(d, 1H), 8.57(s, 1H), 9.58(s, 1H), 10.69(br s, 1H). | Method A, using N-(6-amino-5-chloropyrazin-2-yl)-3-methylisoxazole-4-carboxamide (Preparation 3) and 2,3,5-trichlorophenylboronic acid. |
| 19 | 1-naphthyl | N-[6-amino-5-(1-naphthyl)pyrazin-2-yl]-3-methylisoxazole-4-carboxamide (also known as 3-methyl-isoxazole-4-carboxylic acid (6-amino-5-naphthalen-1-yl-pyrazin-2-yl)-amide) | MS m/z 346[MH]+ $^1$HNMR(d$_6$-DMSO): 2.50(s, 3H), 5.70(br s, 2H), 7.40-7.60(m, 5H), 8.00(m, 2H), 8.70(s, 1H), 9.60(s, 1H). LCMS Rt=2.86min | Method A, using N-(6-amino-5-chloropyrazin-2-yl)-3-methylisoxazole-4-carboxamide (Preparation 3) and 1-naphthalene boronic acid. |
| 20 | 2,5-dichlorophenyl | N-[6-amino-5-(2,5-dichlorophenyl)pyrazin-2-yl]-3-methylisoxazole-4-carboxamide (also known as 3-methyl-isoxazole-4-carboxylic acid [6-amino-5-(2,5-dichlorophenyl)-pyrazin-2-yl]-amide) | MS m/z 366[MH]$^+$ $^1$HNMR(d$_6$-DMSO): 2.40(s, 3H), 6.00(br s, 2H), 7.50-7.60(m, 3H), 8.60(s, 1H), 9.60(s, 1H), 10.65(br s, 1H). | Method A, using N-(6-amino-5-chloropyrazin-2-yl)-3-methylisoxazole-4-carboxamide (Preparation 3) and 2,5-dichlorophenylboronic acid. |
| 21 | 7-chloro-2,3-dihydro-1,4-benzodioxin-5-yl | N-[6-amino-5-(7-chloro-2,3-dihydro-1,4-benzodioxin-5-yl)pyrazin-2-yl]-3-methylisoxazole-4-carboxamide | LCMS Rt=3.21min MS m/z 388[MH]+ | Method C, using 3-(7-chloro-2,3-dihydro-1,4-benzodioxin-5-yl)pyrazine-2,6-diamine (Preparation 13) and 3-methyl-4-isoxazolecarboxylic acid. |

The following examples of the general formula:

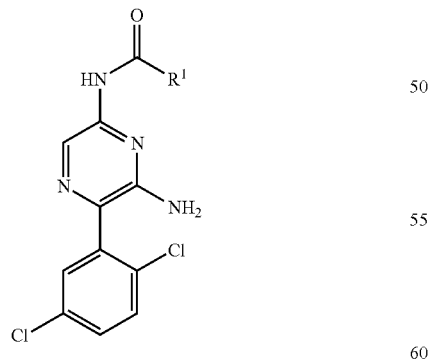

were prepared by methods analogous to Methods B and C, as described above for Examples 2 and 3 using 3-(2,5-dichlorophenyl)pyrazine-2,6-diamine (Preparation 11). Unless otherwise noted, preparation details are as described for the method referred to.

| Example No. | R¹ | Name | Data | Preparation information |
|---|---|---|---|---|
| 22 | isoxazol-3-yl | N-[6-amino-5-(2,5-dichlorophenyl)pyrazin-2-yl]isoxazole-3-carboxamide | LCMS Rt=3.77min MS m/z 350[MH]+ | Method B, using 3-isoxazolecarboxylic acid, 1.5 equivalents lutidine and 1.5 equivalents acid chloride |
| 23 | 4-methyl-1,2,5-oxadiazol-3-yl | N-[6-amino-5-(2,5-dichlorophenyl)pyrazin-2-yl]-4-methyl-1,2,5-oxadiazole-3-carboxamide | MS m/z 363[MH]+ ¹HNMR(CD₃OD): 2.4(3H, s), 7.4-7.6(3H, m), 8.75(1H, s) LCMS Rt=2.56min | Method C, using 4-methyl-1,2,5-oxadiazole-3-carboxylic acid. Acid chloride prepared using neat thionyl chloride at 70° C. |
| 24 | 5-methylisoxazol-4-yl | N-[6-amino-5-(2,5-dichlorophenyl)pyrazin-2-yl]-5-methylisoxazole-4-carboxamide | LCMS Rt=2.28min MS m/z=364[MH]+ | Method B, using 5-methylisoxazole-4-carboxylic acid. Stirred for 1 hour. |
| 25 | 1-(2-methoxyethyl)-1H-pyrazol-5-yl | N-[6-amino-5-(2,5-dichlorophenyl)pyrazin-2-yl]-1-(2-methoxyethyl)-1H-pyrazole-5-carboxamide | LCMS Rt=2.82min MS m/z 407[MH]+ | Method B, using 1-(2-methoxyethyl)-1H-pyrazole-5-carboxylic acid (Preparation 29). |
| 26 | isoxazolyl-4-yl | N-[6-amino-5-(2,5-dichlorophenyl)pyrazin-2-yl]isoxazole-4-carboxamide | LCMS Rt=2.80min MS m/z 350[MH]+ | Method B, using 4-isoxazolecarboxylic acid. |
| 27 | 1-(2-methoxyethyl)-1H-pyrazol-3-yl | N-[6-amino-5-(2,5-dichlorophenyl)pyrazin-2-yl]-1-(2-methoxyethyl)-1H-pyrazole-3-carboxamide | LCMS Rt=2.83min MS m/z 407[MH]+ | Method B, using using 1-(2-methoxyethyl)-1H-pyrazole-3-carboxylic acid (Preparation 30). |

The following examples of the general formula:

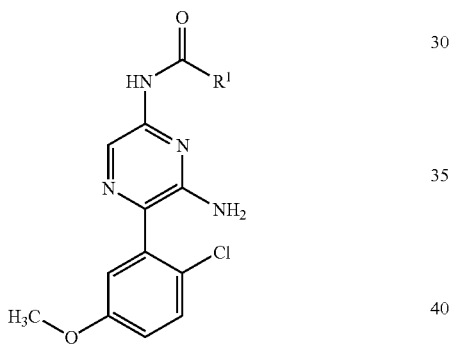

were prepared by methods analogous to Methods B and C, as described above for Examples 2 and 3 using 3-(2-chloro-5-methoxy-phenyl)pyrazine-2,6-diamine (Preparation 6). Unless otherwise noted, preparation details are as described for the method referred to.

| Example No. | R¹ | Name | Data | Preparation information: |
|---|---|---|---|---|
| 28 | 3-methylisoxazol-4-yl | N-[6-amino-5-(2-chloro-5-methoxyphenyl)pyrazin-2-yl]-3-methylisoxazole-4-carboxamide | LCMS Rt=3.46min MS m/z 360[MH]+. | Method C, using 1.5 equivalents acid chloride, prepared from 3-methyl-4-isoxazolecarboxylic acid. |
| 29 | 4-methyl-1,2,5-oxadiazol-3-yl | N-[6-amino-5-(2-chloro-5-methoxyphenyl)pyrazin-2-yl]-4-methyl-1,2,5-oxadiazole-3-carboxamide | LCMS Rt=2.63min MS m/z 360[MH]+ | Method C, using 4-methyl-1,2,5-oxadiazole-3-carboxylic acid. Acid chloride prepared using neat thionyl chloride at 70° C. Amide bond formation left for 2 hours then at room temperature overnight. Another equivalent acid chloride added and reaction left for 4 days. |
| 30 | 5-isopropylisoxazol-4-yl | N-[6-amino-5-(2-chloro-5-methoxyphenyl)pyrazin-2-yl]-5-isopropylisoxazole-4-carboxamide | LCMS Rt=3.40min MS m/z 388[MH]+ | Method B, using 5-isopropyl-isoxazole-4-carboxylic acid. Acid chloride formation left for 1 hour. |

-continued

| Example No. | R¹ | Name | Data | Preparation information: |
|---|---|---|---|---|
| 31 | 3-ethyl-5-methylisoxazol-4-yl | N-[6-amino-5-(2-chloro-5-methoxyphenyl)pyrazin-2-yl]-3-ethyl-5-methylisoxazole-4-carboxamide | LCMS Rt=2.15min MS m/z 388[MH]+ | Method B, using 3-ethyl-5-methylisoxazole-4-carboxylic acid. Acid chloride made using thionyl chloride at 60° C. overnight. |
| 32 | isoxazol-5-yl | N-[6-amino-5-(2-chloro-5-methoxyphenyl)pyrazin-2-yl]isoxazole-5-carboxamide | LCMS Rt=2.66min MS m/z 346[MH]+ | Method B, using isoxazole-5-carboxylic acid. |
| 33 | isoxazol-4-yl | N-[6-amino-5-(2-chloro-5-methoxyphenyl)pyrazin-2-yl]isoxazole-4-carboxamide | LCMS Rt=2.93min MS m/z 345[MH]+ | Method B, using 1.5 equivalents acid chloride prepared from 4-isoxazolecarboxylic acid. |
| 34 | 1-(2-methoxyethyl)-1H-pyrazol-5-yl | N-[6-amino-5-(2-chloro-5-methoxyphenyl)pyrazin-2-yl]-1-(2-methoxyethyl)-1H-pyrazole-5-carboxamide | LCMS Rt=2.98min MS m/z 402[MH]+ | Method B, using 1-(2-methoxyethyl)-1H-pyrazole-5-carboxylic acid (preparation 29). |
| 35 | 1-(2-methoxyethyl)-1H-pyrazol-3-yl | N-[6-amino-5-(2-chloro-5-methoxyphenyl)pyrazin-2-yl]-1-(2-methoxyethyl)-1H-pyrazole-3-carboxamide | LCMS Rt=2.63min MS m/z 403[MH]+ | Method B, using 1-(2-methoxyethyl)-1H-pyrazole-3-carboxylic acid (Preparation 30). |
| 36 | 3,5-dimethylisoxazol-4-yl | N-[6-amino-5-(2-chloro-5-methoxyphenyl)pyrazin-2-yl]-3,5-dimethylisoxazole-4-carboxamide | LCMS Rt=4.3min MS m/z 374[MH]+ | Method C, using 3,5-dimethylisoxazole-4-carboxylic acid. |
| 37 | isoxazol-3-yl | N-[6-amino-5-(2-chloro-5-methoxyphenyl)pyrazin-2-yl]isoxazole-3-carboxamide | LCMS Rt=3.48min MS, m/z 346[MH]+ | Method B, using 1.5 equivalents lutidine and 1.5 equivalents acid chloride, prepared from 3-isoxazolecarboxylic acid. |
| 38 | 5-propylisoxazol-4-yl | N-[6-amino-5-(2-chloro-5-methoxyphenyl)pyrazin-2-yl]-5-propylisoxazole-4-carboxamide | LCMS Rt=2.72min MS m/z 386[MH}+ | Method B, using 5-propyl-4-isoxazolecarboxylic acid. Acid chloride formation left for 1 hour. |

The following examples of the general formula:

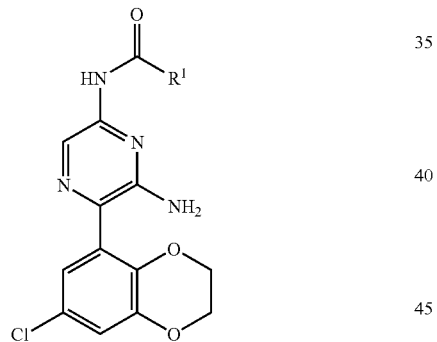

were prepared by methods analogous to Methods B and C, as described above for Examples 2 and 3, using 3-(7-chloro-2,3-dihydro-1,4-benzodioxin-5-yl)pyrazine-2,6-diamine (Preparation 13). Unless otherwise noted, preparation details are as described for the method referred to.

| Example No. | R¹ | Name | Data | Preparation information: |
|---|---|---|---|---|
| 39 | 5-methylisoxazol-4-yl | N-[6-amino-5-(7-chloro-2,3-dihydro-1,4-benzodioxin-5-yl)pyrazin-2-yl]-5-methylisoxazole-4-carboxamide | MS m/z 388, [MH]+ $^1$HNMR($d_6$-DMSO): 2.7(3H, s), 4.25(4H, m), 5.9(2H, br s), 6.85(1H, s), 7.0(1H, s), 8.6(1H, s), 9.2(1H, s), 10.5(1H, br s). LCMS Rt=2.74min | Method B, using 1.5 equivalents lutidine and 1 equivalent acid chloride prepared from 5-methylisoxazole-4-carboxylic acid. |

| Example No. | R¹ | Name | Data | Preparation information: |
|---|---|---|---|---|
| 40 | isoxazol-5-yl | N-[6-amino-5-(7-chloro-2,3-dihydro-1,4-benzodioxin-5-yl)pyrazin-2-yl]isoxazole-5-carboxamide | LCMS Rt=2.82min MS m/z 374[MH]+ | Method B, using isoxazole-5-carboxylic acid. |
| 41 | 4-methyl-1,2,5-oxadiazol-3-yl | N-[6-amino-5-(7-chloro-2,3-dihydro-14-benzodioxin-5-yl)pyrazin-2-yl]-4-methyl-1,2,5-oxadiazole-3-carboxamide | LCMS Rt=3.10min MS m/z 389[MH]+ | Method B, using 4-methyl-1,2,5-oxadiazole-3-carboxylic acid. Acid chloride prepared using neat thionyl chloride at 70° C. |
| 42 | isoxazol-4-yl | N-[6-amino-5-(7-chloro-2,3-dihydro-1,4-benzodioxin-5-yl)pyrazin-2-yl]isoxazole-4-carboxamide | LCMS Rt=3.11min MS m/z 374[MH]+ | Method B, using 4-isoxazolecarboxylic acid. |
| 43 | isoxazol-3-yl | N-[6-amino-5-(7-chloro-2,3-dihydro-1,4-benzodioxin-5-yl)pyrazin-2-yl]isoxazole-3-carboxamide | LCMS Rt=3.07min MS m/z 373[MH]+ | Method B, using 3-isoxazolecarboxylic acid. |

The following examples of the general formula:

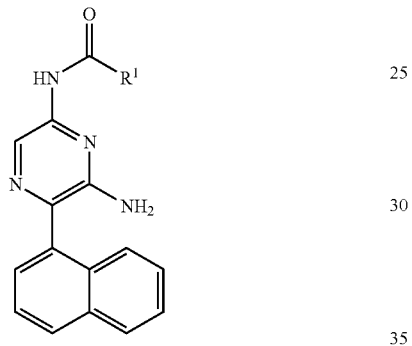

were prepared by methods analogous to Methods B and C, as described above for Examples 2 and 3, using 3-(1-naphthyl)pyrazine-2,6-diamine (Preparation 8). Unless otherwise noted, preparation details are as described for the method referred to.

| Example No. | R¹ | Name | Data | Preparation information |
|---|---|---|---|---|
| 44 | 4-methyl-1,2,5-oxadiazol-3-yl | N-[6-amino-5-(1-naphthyl)pyrazin-2-yl]-4-methyl-1,2,5-oxadiazole-3-carboxamide | LCMS Rt=2.76min MS m/z 346[MH]+ | Method B, using 4-methyl-1,2,5-oxadiazole-3-carboxylic acid. Acid chloride prepared using neat thionyl chloride at 70° C. Amide bond formation left for 4 days. |
| 45 | isoxazol-3-yl | N-[6-amino-5-(1-naphthyl)pyrazin-2-yl]isoxazole-3-carboxamide | LCMS Rt=3.65min MS m/z 332[MH]+ | Method B, using 3-isoxazolecarboxylic acid. |
| 46 | 1-methyl-1H-pyrazol-5-yl | N-[6-amino-5-(1-naphthyl)pyrazin-2-yl]-1-methyl-1H-pyrazole-5-carboxamide | MS m/z 345[MH]+ $^1$HNMR(d$_6$-DMSO): 4.1(s, 3H), 5.7(br s, 2H), 7.3(m, 1H), 7.4-7.6(m, 5H), 8.0(m, 2H), 8.7(s, 1H). LCMS Rt=2.72min | Method C, using 1-methyl-1H pyrazole-5-carboxylic acid. |

The following examples of the general formula:

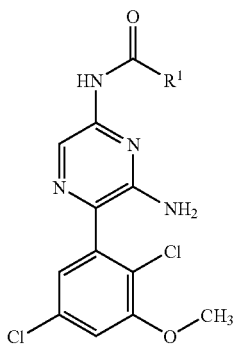

were prepared by methods analogous to Method B, as described above for Examples 2, using 3-(2,5-dichloro-3-methoxyphenyl)pyrazine-2,6-diamine (Preparation 9). Unless otherwise noted, preparation details are as described for the method referred to.

was added and the reaction was left to stir at room temperature for 3 hours before concentrating in vacuo and azeotroping with dichloromethane. The residue was dissolved in $CH_3CN$ (3.93 ml) to afford a 1M solution. The 1M solution of the resulting acid chloride (0.526 ml, 0.526 mmole) was added to a solution of 3-(2,5-dichloro-3-methoxyphenyl)pyrazine-2,6-diamine (Preparation 9, 0.15 g, 0.526 mmol) and lutidine (89 μl, 0.787 mmol) in $CH_3CN$ (10 ml). The reaction was stirred at room temperature for 4 days before concentrating in vacuo. The residue was taken up in 10 ml dichloromethane, washed with 5 ml water, and the two layers were separated using a phase separation cartridge. The organic layer was concentrated in vacuo to afford a cream solid. The residue was purified by silica gel column chromatography, eluting with ethyl acetate:heptane 1:1, to afford 62 mg of the title product as a white solid/foam.

MS m/z 394 [MH]+

$^1$HNMR ($d_6$-DMSO): 2.4 (s, 3H), 3.9 (s, 3H), 6.0 (br s, 2H), 7.0 (m, 1H), 7.3 (m, 1H), 8.6 (s, 1H), 9.6 (s, 1H), 10.65 (br s, 1H).

LCMS Rt=2.85 min

| Example No. | R$^1$ | Name | Data | Preparation information |
|---|---|---|---|---|
| 47 | 4-methyl-1,2,5-oxadiazol-3-yl | N-[6-amino-5-(2,5-dichloro-3-methoxyphenyl)pyrazin-2-yl]-4-methyl-1,2,5-oxadiazole-3-carboxamide | LCMS Rt=3.43min MS m/z 394[MH]+ | Method B, using 4-methyl-1,2,5-oxadiazole-3-carboxylic acid. Acid chloride prepared using neat thionyl chloride at 70° C. Amide bond formation left for 4 days |
| 48 | isoxazol-4-yl | N-[6-amino-5-(2,5-dichloro-3-methoxyphenyl)pyrazin-2-yl]isoxazole-4-carboxamide | LCMS Rt=3.11min MS m/z 379[MH]+ | Method B, using 4-isoxazolecarboxylic acid. Amide bond formation left for 4 days. |

EXAMPLE 49

N-[6-Amino-5-(2,5-dichloro-3-methoxyphenyl)pyrazin-2-y]-3-methylisoxazole-4-carboxamide

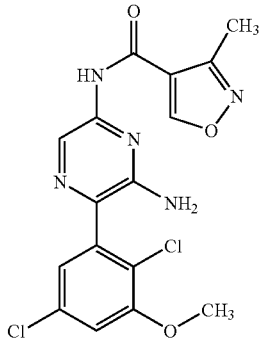

Oxalyl chloride (515 μl, 5.90 mmol) was added to a slurry of 3-methyl-4-isoxazolecarboxylic acid (500 mg, 3.93 mmol) in dichloromethane (10 ml). One drop of dimethylformamide The following examples of the general formula:

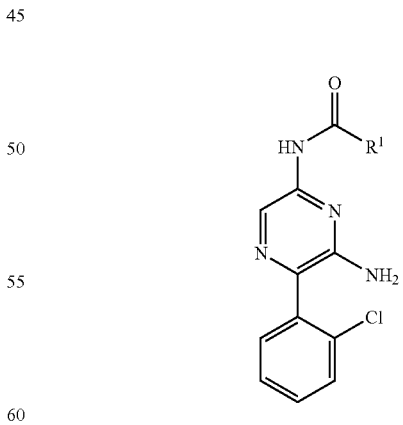

were prepared by methods analogous to Methods A and B, as described above for Examples 1 and 2. Unless otherwise noted, preparation details are as described for the method referred to.

| Example No. | R1 | Name | Data | Preparation information |
|---|---|---|---|---|
| 50 | 5-methylisoxazol-4-yl | N-[6-amino-5-(2-chlorophenyl)pyrazin-2-yl]-5-methylisoxazole-4-carboxamide | LCMS Rt=3.00min MS m/z 330[MH]+ | Method B, using 3-(2-chlorophenyl)pyrazine-2,6-diamine (Preparation 10) and 5-methylisoxazole-4-carboxylic acid. Acid chloride formation left for 1 hour. |
| 51 | 5-isopropylisoxazol-4-yl | N-[6-amino-5-(2-chlorophenyl)pyrazin-2-yl]-5-isopropylisoxazole-4-carboxamide | LCMS Rt=3.17min MS m/z 358[MH]+ | Method B, using 3-(2-chlorophenyl)pyrazine-2,6-diamine (Preparation 10) and 5-isopropylisoxazole-4-carboxylic acid. |
| 52 | isoxazol-3-yl | N-[6-amino-5-(2-chlorophenyl)pyrazin-2-yl]isoxazole-3-carboxamide | LCMS Rt=2.96min MS m/z 316[MH]+ | Method B, using 3-(2-chlorophenyl)pyrazine-2,6-diamine (Preparation 10) and 3-isoxazolecarboxylic acid. Acid chloride formation left for 1 hour. Acylation left for 3 hours. |
| 53 | isoxazol-5-yl | N-[6-amino-5-(2-chlorophenyl)pyrazin-2-yl]isoxazole-5-carboxamide | LCMS Rt=3.05min MS m/z 316[MH]+ | Method B, using 3-(2-chlorophenyl)pyrazine-2,6-diamine (Preparation 10) and isoxazole-5-carboxylic acid. Acid chloride formation left for 1 hour. Acylation left for 3 hours. |
| 54 | isoxazol-4-yl | N-[6-amino-5-(2-chlorophenyl)pyrazin-2-yl]isoxazole-4-carboxamide | LCMS Rt=2.84 MS m/z 316[MH]+ | Method B, using 3-(2-chlorophenyl)pyrazine-2,6-diamine (Preparation 10) and 4-isoxazolecarboxylic acid. Acid chloride formation left for 1 hour. Acylation left for 2 hours. |
| 55 | 4-methyl-1,2,5-oxadiazol-3-yl | N-[6-amino-5-(2-chlorophenyl)pyrazin-2-yl]-4-methyl-1,2,5-oxadiazole-3-carboxamide | LCMS Rt=3.23min MS m/z 331[MH]+ | Method B, using 3-(2-chlorophenyl)pyrazine-2,6-diamine (Preparation 10) and 4-methyl-1,2,5-oxadiazole-3-carboxylic acid. Acid chloride prepared using neat thionyl chloride at 70° C. |
| 56 | 1-(2-methoxyethyl)-1H-pyrazol-5-yl | N-[6-amino-5-(2-chlorophenyl)pyrazin-2-yl]-1-(2-methoxyethyl)-1H-pyrazole-5-carboxamide | LCMS Rt=2.86 MS m/z 373[MH]+ | Method B, using 3-(2-chlorophenyl)pyrazine-2,6-diamine (Preparation 10) and 1-(2-methoxyethyl)-1H-pyrazole-5-carboxylic acid (preparation 29) Acid chloride formation left for 1 hour. |
| 57 | 1-methyl-1H-pyrazol-5-yl | N-[6-amino-5-(2-chlorophenyl)pyrazin-2-yl]-1-methyl-1H-pyrazole-5-carboxamide | LCMS Rt=2.75min MS m/z 329[MH]+ | Method A, using N-(6-amino-5-chloropyrazin-2-yl)-1-methyl-1H-pyrazole-5-carboxamide (Preparation 2) and 2-chlorophenylboronic acid. | the following examples of the general formula:

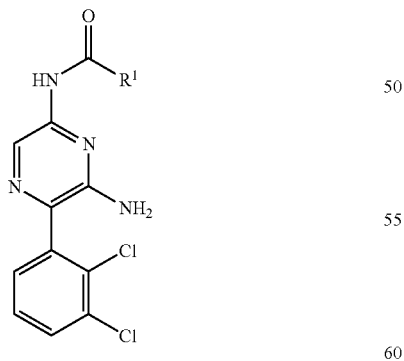

were prepared by methods analogous to Method B, as described above for Example 2, using 3-(2,3-dichlorophenyl)pyrazine-2,6-diamine (Preparation 7). Unless otherwise noted, preparation details are as described for the method referred to.

| Example No. | R[1] | Name | Data | Preparation information |
|---|---|---|---|---|
| 58 | 1-(2-methoxyethyl)-1H-pyrazol-5-yl | N-[6-amino-5-(2,3-dichlorophenyl)pyrazin-2-yl]-1-(2-methoxyethyl)-1H-pyrazole-5-carboxamide | LCMS Rt=3.09min MS m/z 406[MH]+ | Method B, using 1-(2-methoxyethyl)-1H-pyrazole-5-carboxylic acid (Preparation 29). Amide bond formation left for 4 days |
| 59 | 4-methyl-1,2,5-oxadiazol-3-yl | N-[6-amino-5-(2,3-dichlorophenyl)pyrazin-2-yl]-4-methyl-1,2,5-oxadiazole-3-carboxamide | LCMS Rt=3.37min MS m/z 364{MH]+ | Method B, using 4-methyl-1,2,5-oxadiazole-3-carboxylic acid. Acid chloride prepared using neat thionyl chloride at 70° C. Amide bond formation left for 4 days |
| 60 | isoxazol-4-yl | N-[6-amino-5-(2,3-dichlorophenyl)pyrazin-2-yl]isoxazole-4-carboxamide | LCMS Rt=3.02min MS m/z 349[MH]+ | Method B, using 4-isoxazolecarboxylic acid. Amide bond formation left for 18 hours |

EXAMPLE 61

N-[6-amino-5-(2,3,5-trichlorophenyl)pyrazin-2-yl]isoxazole-3-carboxamide

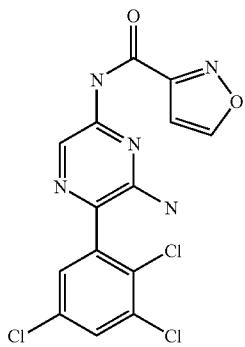

N-[6-amino-5-(2,3,5-trichlorophenyl)pyrazin-2-yl]isoxazole-3-carboxamide was prepared by a method analogous to Method B, as described above for Example 2, using 3-isoxazolecarboxylic acid and 3-(2,3,5-trichlorophenyl)pyrazine-2,6-diamine (Preparation 12).

LCMS Rt=4.07 min
MS m/z 386 [MH]+

EXAMPLE 62

N-[6-amino-5-(2,5-dichlorophenyl)pyrazin-2-yl]-1H-pyrazole-5-carboxamide

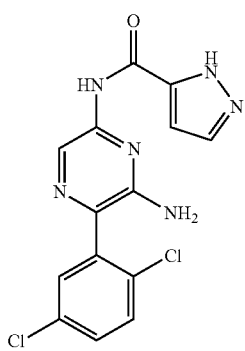

Oxalyl chloride (0.17 ml, 1.9 mmol) was added to a slurry of 2-(2-trimethylsilanylmethoxy-ethyl)-2H-pyrazole-3-carboxylic acid) (Heterocycles (1992) 34 303-314), (428 mg, 1.76 mmol) in dichloromethane (15 ml), 1 drop of dimethylformamide was added and the reaction stirred at room temperature under $N_2$ for 1 hour before concentrating in vacuo and azeotroping with dichloromethane. The resulting acid chloride was dissolved in 5 ml acetonitrile and added to a solution of 3-(2,5-dichloro-phenyl)pyrazine-2,6-diamine (Preparation 11, 300 mg, 1.18 mmol) in acetonitrile (15 ml) and 2,6-lutidine (0.21 ml, 1.8 mmol). The reaction was stirred at room temperature under $N_2$ for 72 hours before concentrating in vacuo then partitioning between 50 ml ethyl acetate and 50 ml water. The organic layer was dried over $MgSO_4$ and concentrated in vacuo to give a brown oil which was purified by column chromatography (ethyl acetate, heptane, 1:2) to give 52 mg of the title product.

$^1$HNMR (CD$_3$OD) 0.00 (s, 9H), 1.90 (t, 2H), 3.65 (t, 2H), 5.55 (s, 2H), 6.95 (s, 1H), 7.45-7.55 (m, 3H), 7.90 (s, 1H), 8.80 (s, 1H).

To a suspension of the above acylation product (10 mg, 0.21 mmol) in tetrahydrofuran (3 ml) was added tetrabutylammoniumfluoride (0.022 ml, 0.0212 mmol, 1.0M soln in tetrahydrofuran) and reaction heated to 65° C. for 2 hours. The reaction mixture was concentrated in vacuo and the residue partitioned between 5 ml ethyl acetate and 5 ml water. The organic was dried over $MgSO_4$ and concentrated in vacuo. The resulting residue was dissolved in 1 ml dimethylsulfoxide and purified by preparative HPLC.

LCMS Rt=2.04 min
MS m/z 349 [MH]+

The following Preparations illustrate the preparation of certain intermediates used to prepare the above Examples.

Preparation 1

3-Chloro-pyrazine-2,6-diamine

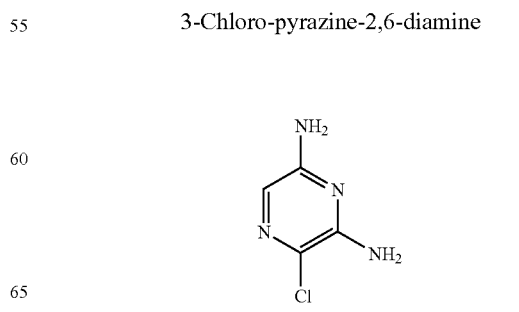

Lithium hydroxide (12.4 g, 0.30 mol) was added to a stirred suspension of 3,5-diamino-6-chloro-pyrazine-2-carboxylic acid methyl ester (20 g, 99 mmol) in methanol (300 ml) and water (120 ml) and the reaction heated at 90° C. for 1.5 hours before allowing to cool to room temperature. The reaction was concentrated in vacuo to afford a yellow slurry and this was suspended in 1,4-dioxane (350 ml) and 2M aqueous HCl solution (200 ml) was added. The mixture was heated at 100° C. for 2 hours and then allowed to cool before removing the 1,4-dioxane in vacuo. The resulting aqueous solution was taken to pH 8 using sodium carbonate (saturated aqueous) and extracted into ethyl acetate (3×300 ml). The combined organic layers were washed with brine (300 ml), dried ($Na_2SO_4$) and concentrated in vacuo to afford a yellow solid (11.7 g, 82%).

$^1$HNMR ($d_6$-DMSO): 5.95 (br s, 2H), 6.02 (br s, 2H), 6.82 (s, 1H).

MS m/z 147 [MH]$^+$

Preparation 2

N-(6-Amino-5-chloropyrazin-2-yl)-1-methyl-1H-pyrazole-5-carboxamide

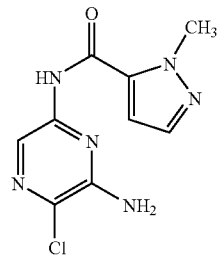

Oxalyl chloride (0.288 ml, 3.32 mmol) was added to a suspension of 1-methyl-1H-pyrazole-5-carboxylic acid (0.279 g, 2.21 mmol) in dichloromethane (5 ml) followed by 1 drop of dimethylformamide. The mixture was stirred at room temperature for 4 hours before concentrating in vacuo and azeotroping with dichloromethane. The residue was taken up in pyridine (1 ml) and added to a solution of 3-chloro-pyrazine-2,6-diamine (Preparation 1) (0.16 g, 1.11 mmol) and the mixture heated at 60° C. for 3 hours before cooling to room temperature and concentrating in vacuo. The residue was purified by silica gel column chromatography, eluting with ethylacetate:heptane 1:1, to afford the product as a pale solid (100 mg).

$^1$HNMR ($d_6$-DMSO): 4.05 (s, 3H), 6.60 (br s, 2H), 7.20 (d, 1H), 7.50 (d, 1H), 8.30 (s, 1H), 10.60 (br s, 1H).

MS m/z 255 [MH]$^+$

Preparation 3

N-(6-Amino-5-chloropyrazin-2-yl)-3-methylisoxazole-4-carboxamide

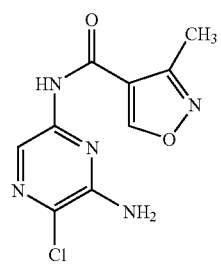

Oxalyl chloride (0.06 ml, 0.69 mmol) was added to a solution of 3-Methyl-isoxazole-4-carboxylic acid (0.06 g, 0.48 mmol) followed by 1 drop of dimethylformamide. The mixture was stirred at room temperature for 4 hours before concentrating in vacuo and azeotroping with dichloromethane. The residue was taken up in pyridine (1 ml) and added to a solution of 3-chloro-pyrazine-2,6-diamine (Preparation 1) (0.035 g, 0.24 mmol) in anhydrous pyridine (3 ml) and the mixture heated at 50° C. for 3 hours before cooling to room temperature and concentrating to dryness in vacuo. The residue was purified by silica gel column chromatography, eluting with ethyl acetate:heptane 1:1, to afford the product as a white solid (30 mg).

$^1$HNMR ($d_6$-DMSO): 2.40 (s, 3H), 6.60 (br s, 2H), 8.35 (s, 1H), 9.60 (s, 1H), 10.65 (br s, 1H).

LCMS Rt=2.35 min

MS m/z 254 [MH]$^+$

Preparation 4

N-(6-Amino-5-chloropyrazin-2-yl)-5-methylisoxazole-4-carboxamide

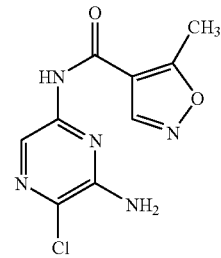

Oxalyl chloride (0.8 ml, 10.3 mmol) was added to a solution of 5-Methyl-isoxazole-4-carboxylic acid (1 g, 6.9 mmol) in dichloromethane (30 ml) followed by 1 drop of dimethylformamide. The mixture was stirred at room temperature for 5 hours before concentrating in vacuo and azeotroping with dichloromethane. The residue was taken up in pyridine (3 ml) and added to a solution of 3-chloro-pyrazine-2,6-diamine (Preparation 1) (0.65 g, 4.6 mmol) in anhydrous pyridine (30 ml) and the mixture heated at 50° C. for 3 hours before cooling to room temperature and concentrating in vacuo. The residue was purified by silica gel column chromatography, eluting with ethyl acetate:heptane 1:1, to afford the product as a white solid (360 mg).

$^1$HNMR ($d_6$-DMSO): 2.51 (s, 3H), 6.71 (br, s, 2H), 8.35 (s, 1H), 9.12 (s, 1H), 10.63 (br, s, 1H).

MS m/z 254 [MH]$^+$

Preparation 5

3,5-Diamino-6-(2-chloro-5-methoxy-phenyl)-pyrazine-2-carboxylic acid methyl ester

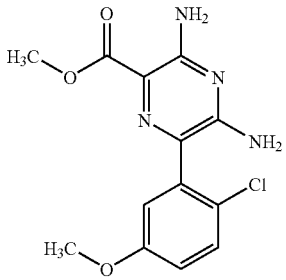

Method D

To a suspension of 3,5-diamino-6-chloro-pyrazine-2-carboxylic acid methyl ester (10.9 g, 53.7 mmol) in 220 ml 1,4-dioxane and water (40 ml) was added 2-chloro-5-methoxybenzene boronic acid (20 g, 107 mmol), cesium carbonate (17.5 g, 53.7 mmol) and palladium tetrakis(triphenylphosphine) (620 mg, 0.54 mmol). The reaction was heated in an oil bath at 70-75° C. for 2 hours. The reaction was then cooled and poured into 500 ml water. The resulting slurry was stirred for 10 minutes before filtering under vacuum. The beige solid collected was then slurried in 100 ml methanol, stirred for 15 minutes, then filtered, washing the filter cake with methanol and vacuum drying to afford 17.4 g of the title product.

$^1$HNMR (d$_6$-DMSO): NMR (DMSO): 3.65 (s, 3H), 3.75 (s, 3H), 6.4 (br s 2H), 6.9 (d, 1H), 7.0 (dd, 1H), 7.05 (br, s, 2H), 7.4 (d, 2H).

LCMS Rt=3.74 min

MS m/z 309 [MH]+

Preparation 6

3-(2-Chloro-5-methoxy-phenyl)-pyrazine-2,6-diamine

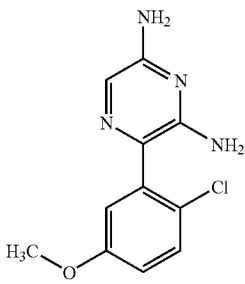

Method E

To a suspension of 3,5-diamino-6-(2-chloro-5-methoxyphenyl)-pyrazine-2-carboxylic acid methyl ester (Preparation 5, 16.5 g, 53.4 mmol) in 255 ml methanol and 76 ml water was added LiOH (6.7 g, 160 mmol), and the reaction was stirred at 90° C. for 2 hours. The reaction was concentrated in vacuo to dryness. The residue was slurried in 380 ml 1,4-dioxane, and 230 ml 2N HCl was added. The reaction was heated to 100° C. for 1 hour before cooling to room temperature and concentrating in vacuo. The residue was basified with 880 NH$_3$ and extracted into 2×300 ml ethylacetate. The organic layers were combined, dried with MgSO$_4$ and concentrated in vacuo. The solid residue was triturated with diethylether and filtered to afford 10 g of a buff solid.

$^1$HNMR (d$_6$-DMSO): 3.25 (3H, s), 5.2 (br, s, 2H), 5.9 (br, s, 2H), 6.8 (d, 1H), 6.9 (dd, 1H), 7.15 (s, 1H), 7.4 (d, 1H).

LCMS Rt=2.92 min

MS m/z 251 [MH]+

Preparation 7

3-(2,3-Dichlorophenyl)-pyrazine-2,6-diamine

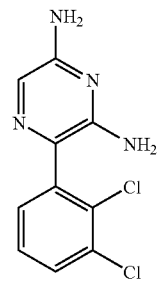

Method F

Potassium cyanide (500 mg, 7.7 mmol) and 2-aminoacetamidine dihydrobromide (1.77 g, 7.5 mmol) were stirred in methanol (15 ml) at room temperature for 1 hour. 2,3-Dichlorobenzaldehyde (1.34 g, 7.68 mmol) was added and the suspension was stirred at room temperature overnight. Lithium hydroxide monohydrate (1.0 g, 23.8 mmol) was added and the mixture was stirred whilst open to the atmosphere at room temperature for 24 hours. The reaction mixture was partitioned between ethyl acetate (80 ml) and water (50 ml). The ethyl acetate solution was washed with water (30 ml), then dried over anhydrous sodium sulphate and evaporated in vacuo to give a light brown gum. This was purified using silica gel column chromatography, eluting with ethyl acetate, to furnish 370 mg of the title product as a brown gum.

$^1$HNMR (CDCl$_3$): 4.26 (br s, 2H), 4.43 (br s, 2H), 7.26 (d, 1H), 7.31 (m, 1H), 7.46 (s, 1H), (7.50 (d, 1H)

MS m/z 257 [MH]+

The following intermediates of the general formula:

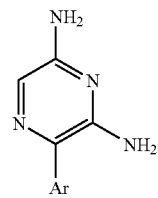

were made by a two step method analogous to Method D followed by Method E. Unless otherwise noted, preparation details are as described above for Preparations 5 and 6.

| Preparation No. | Name | Data | Preparation information |
|---|---|---|---|
| 8 | 3-(1-naphthyl)pyrazine-2,6-diamine | MS m/z 237[MH]+<br>$^1$HNMR($d_6$-DMSO): 5.1(2H, br, s), 5.9(2H, br, s), 7.25(1H, s), 7.4-7.6(5H, m), 7.9(2H, m). | Method D, using 1-napthaleneboronic acid.<br>Method E, using 3 equivalents LiOH, at 75° C. for 5 hours, followed by 1N HCl for 2.5 hours. |
| 9 | 3-(2,5-dichloro-3-methoxyphenyl)pyrazine-2,6-diamine | MS m/z 285[MH]+<br>$^1$HNMR(CDCl$_3$): 3.95(s, 3H), 4.35(br s, 2H), 4.5(br s, 2H), 6.95(s, 1H), 7.0(s, 1H), 7.5(s, 1H). | Method D, using 2-(2,5-dichloro-3-methoxyphenyl)-4,4,5,5-tetramethyl-[1,3,2]dioxaborolane (Preparation 20). Method E, using 5 equivalents of LiOH at 90° C. for 1 hour, followed by 2M HCl at 100° C. for 2 hours. |
| 10 | 3-(2-chlorophenyl)pyrazine-2,6-diamine | MS m/z 221[MH]+<br>$^1$HNMR($d_6$-DMSO): 5.20(br s, 2H), 5.90(br s, 2H), 7.15(s, 1H), 7.30-7.40(m, 3H), 7.45-7.50(m, 1H)<br>LCMS Rt=2.01min | Method D, using 2-chlorophenylboronic acid. |
| 11 | 3-(2,5-dichlorophenyl)pyrazine-2,6-diamine | MS m/z 255[MH]+<br>$^1$HNMR($d_6$-DMSO): 5.49(2H, br s), 6.03(2H, br s), 7.15(1H, s), 7.36(1H, s), 7.42(1H, d), 7.52(1H, d) | Method D, using 2,5-dichlorophenylboronic acid. |
| 12 | 3-(2,3,5-trichlorophenyl)pyrazine-2,6-diamine | MS m/z 289[MH]+<br>$^1$H NMR(CDCl$_3$) 4.23(2H, br s), 4.41(2H, br s), 7.35(1H, s), 7.45(1H, s), 7.50(1H, s) | Method D, using 10 mol % palladium tetrakis(triphenylphosphine) and 2,3,5-trichlorophenylboronic acid. |
| 13 | 3-(7-chloro-2,3-dihydro-1,4-benzodioxin-5-yl)pyrazine-2,6-diamine | MS m/z 279[MH]+<br>$^1$H NMR(CDCl$_3$): 4.28(4H, m), 4.40(2H, br s), 4.46(2H, br s), 6.91(1H, s), 6.95(1H, s), 7.47 | Method D, using 10 mol % palladium tetrakis(triphenylphosphine) and (7-chloro-2,3-dihydro-1,4-benzodioxin-5-yl)boronic acid (Preparation 23). 1.5 Equivalents of LiOH were used for the ester hydrolysis (Method E). |

Preparation 14

3-(2,3-Dichloro-6-methoxyphenyl)pyrazine-2,6-diamine

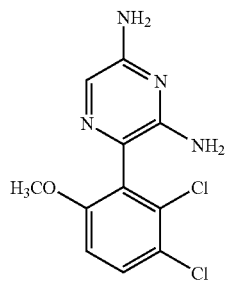

3-(2,3-Dichloro-6-methoxyphenyl)pyrazine-2,6-diamine was prepared by a method analogous to Method F as described above for Preparation 7 and using 2,3-dichloro-6-methoxybenzaldehyde (Preparation 27). The reaction was stirred for 5 hours with LiOH/air.

$^1$HNMR (CDCl$_3$): 3.76 (s, 3H), 4.12 (br s, 2H), 4.35 (br s, 2H), 6.86 (d, 1H), 7.47 (d, 1H), 7.52 (s, 1H)

MS m/z 287 [MH]+

Preparation 15

3-(2-chloro-3-methoxyphenyl)pyrazine-2,6-diamine

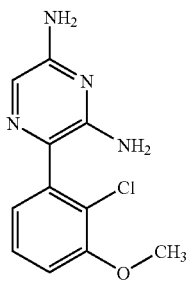

3-(2-chloro-3-methoxyphenyl)pyrazine-2,6-diamine was prepared by a method analogous to Method F as described above for Preparation 7 and using 2-chloro-3-methoxybenzaldehyde.

NMR (CD$_3$OD): 3.9 (3H, s), 6.95 (1H, m), 7.15 (1H, m), 7.2 (1H, s), 7.35 (1H, m)

MS m/z 251 [MH]+

Preparation 16

1-Bromo-3-chloro-5-methoxybenzene

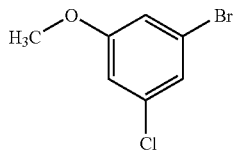

To a solution of 1-bromo-3-chloro-5-fluorobenzene (25 g, 0.12 mol) in methanol (800 ml) was added sodium methoxide (64 g, 1.18 mol). The reaction was heated to reflux for 9 days. The reaction was then concentrated in vacuo to one fifth of the volume (150 ml), cooled and water (1000 ml) added. The mixture was extracted with diethyl ether (3×150 ml). The organic layer was washed with brine (2×100 ml), dried ($Na_2SO_4$) and evaporated to afford the title product (24.6 g).

$^1$HNMR ($CDCl_3$): 3.80 (s, 3H), 6.84 (s, 1H), 6.96 (s, 1H), 7.10 (s, 1H).

GC-MS m/z 222 [MH]$^+$, Rt=3.86 min

Preparation 17

1-Bromo-2,3-dichloro-5-methoxybenzene

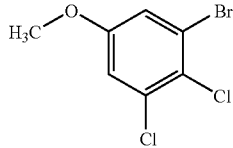

1-Bromo-3-chloro-5-methoxybenzene (Preparation 16, 6.0 g, 27 mmol) and trichloroisocyanuric acid (2.3 g, 9.9 mmol) were stirred in dimethylformamide (100 ml) at 50° C. for 3 hours. n-Heptane was added and the mixture filtered to remove insoluble impurities. The mixture was then concentrated in vacuo and the residue purified by silica gel column chromatography, eluting with n-heptane:ethyl acetate 9:1, to afford the title product as a white solid (5.0 g).

$^1$HNMR ($CDCl_3$): 3.80 (s, 3H), 7.00 (s, 1H), 7.20 (s, 1H).
GC-MS m/z 256 [MH]$^+$, Rt=4.60 min

Preparation 18

2,(2,3-Dichloro-5-methoxy-phenyl-4,4,5,5-tetramethyl-[1,3,2]dioxaborolane

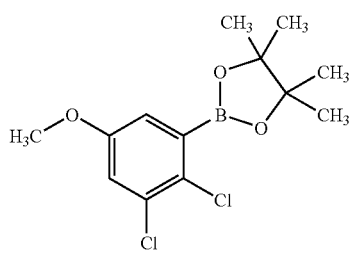

1-Bromo-2,3-dichloro-5-methoxybenzene (Preparation 17, 1.3 g, 5.1 mmol), bis(pinacolato)diboron (1.4 g, 5.6 mmol), potassium acetate (1.5 g, 15 mmol) and 1,1'-[bis(diphenylphosphino)ferrocene]dichloropalladium (II) (0.37 g, 0.51 mmol) were combined and stirred in dimethylsulfoxide (10 ml) for 5 hours at 83° C. in a sealed vessel. The mixture was then poured onto ice and extracted with diethyl ether. The organic layer was dried and evaporated. The residue was stirred in n-heptane, filtered and evaporated. This reaction was performed three times and the crude material combined for purification by silica gel column chromatography, eluting with n-heptane:ethyl acetate 9:1, to afford the product as a yellow oil (3.1 g).

$^1$HNMR ($CDCl_3$): 1.40 (s, 12H), 3.80 (s, 3H), 7.08 (s, 1H), 7.10 (s, 1H).

GC-MS m/z 304 [MH]$^+$, Rt=5.78 min

Preparation 19

1-Bromo-2,5-dichloro-3-methoxybenzene

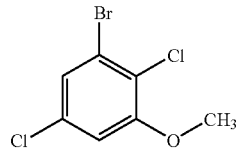

1-Bromo-2,5-dichloro-3-fluorobenzene (40 g, 0.16 mol) and sodium methoxide (44.3 g, 0.82 mol) were stirred in methanol (500 ml) at the reflux temperature for 16 hours. The reaction was cooled to ambient temperature then quenched with water (500 ml). The mixture was extracted with diethyl ether (3×300 ml), dried ($Na_2SO_4$) and evaporated to afford the product as a white solid (40 g)

$^1$HNMR ($CDCl_3$): 3.90 (s, 3H), 6.86 (d, 1H), 7.26 (d, 1H).
MS m/z 256 [MH]$^+$
GC-MS m/z 256 [MH]$^+$, Rt=4.58 min

Preparation 20

2-(2,5-Dichloro-3-methoxy-phenyl)-4,4,5,5-tetramethyl-[1,3,2]dioxaborolane

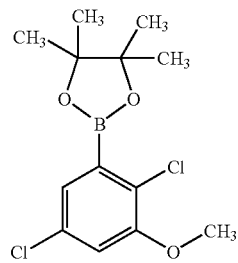

1-Bromo-2,5-dichloro-3-methoxybenzene (Preparation 19, 10 g, 39 mmol), bis(pinacolato)diboron (10.9 g, 43 mmol), potassium acetate (11.5 g, 117 mmol) and 1,1'-[bis(diphenylphosphino)ferrocene]dichloropalladium (II) (2.8 g, 4.0 mmol) were combined and stirred in dimethylsulfoxide (100 ml). The reaction flask was purged with nitrogen for 5 minutes before heating to 80° C. for 16 hours. The mixture was cooled and the dimethylsulfoxide removed in vacuo. The residue was partitioned between water (500 ml) and dichloromethane (3×200 ml). The organic layer was washed with brine (300 ml), dried (Na$_2$SO$_4$) and evaporated to give a black oil. The residue was dissolved in diethylether (200 ml) and filtered over a plug of silica to afford a green oil. This was purified using silica gel column chromatography, eluting with heptane:diethyl ether 7:1, to furnish 5.6 g of the title product as a white solid.

$^1$HNMR (CDCl$_3$): 1.40 (s, 12H), 3.89 (s, 1H), 6.98 (s, 1H), 7.20 (s, 1H).

GC-MS m/z 304 [MH]$^+$, Rt=5.75 min

Preparation 21

3-Bromo-5-chloro-benzene-1,2-diol

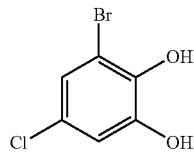

To a stirred suspension of 3-bromo-5-chloro-2-hydroxybenzaldehyde (49.5 g, 0.21 mol) in 0.5N aqueous NaOH (500 ml, 0.25 mol) at 40° C. was added dropwise hydrogen peroxide (21.4 g of a 35% aqueous solution, 0.22 mol) over 15 minutes and the resultant mixture stirred for 16 hours. The mixture was cooled to room temperature, diluted with 1 N aqueous NaOH (200 ml) and washed with diethyl ether (3×300 ml). The aqueous layer was acidified with concentrated HCl to pH 2 and extracted with Et$_2$O (3×200 ml). The organic extracts were combined, washed with brine, dried (Na$_2$SO$_4$), filtered and concentrated in vacuo to afford the desired product as a red/brown solid (46.0 g, 99%).

$^1$HNMR (CDCl$_3$): 5.40 (s, 1H), 5.55 (br s, 1H), 6.88 (d, 1H), 7.05 (d, 1H).

MS m/z 224 [MH]$^+$

MP 71-73° C.

Preparation 22

5-Bromo-7-chloro-2,3-dihydro-benzo[1,4]dioxine

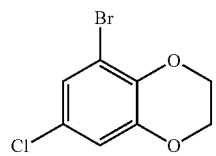

To a solution of 1,2-dibromoethane (1.44 ml, 16 mmol) and tetrabutylammonium bromide (96 mg, 2.5 mol %) in water (8 ml) at reflux under nitrogen was added a mixture of 3-bromo-5-chloro-benzene-1,2-diol (Preparation 21, 2.68 g, 12 mmol) and NaOH (1.06 g, 26.2 mmol) in water (10 ml) over 4 hours, and the resultant mixture stirred overnight. The reaction mixture was cooled to room temperature and diluted with water (100 ml). The mixture was extracted with Et$_2$O (3×100 ml), and the combined organic extracts were concentrated in vacuo. Purification by flash chromatography (pentane:dichloromethane 9:1) afforded the desired product as a yellow oil (1.78 g, 60%) which crystallised on standing to a yellow solid.

$^1$HNMR (CDCl$_3$): 4.27 (t, 2H), 4.35 (t, 2H), 6.86 (d, 1H), 7.10 (d, 1H).

MP 56.5-58.0° C.

Preparation 23

(7-Chloro-2,3-dihydro-1,4-benzodioxin-5-yl)boronic acid

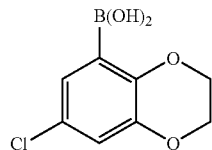

To a stirred solution of 5-bromo-7-chloro-2,3-dihydrobenzo[1,4]dioxine (Preparation 22, 1.5 g, 6 mmol) in dry Et$_2$O (45 ml) under nitrogen at −70° C. was added n-butyl lithium (2.63 ml of a 2.5M solution in hexane, 6.6 mmol) and the resultant mixture stirred for 1 hr. Trimethyl borate (0.92 ml, 8 mmol) was then added and the mixture stirred at room temperature overnight. Saturated aqueous NH$_4$Cl was added (60 ml) and the aqueous layer extracted with Et$_2$O (3×100 ml). The combined organic extracts were concentrated in vacuo. The residue was taken up in 1M aqueous NaOH and washed with Et$_2$O (100 ml). The aqueous layer was then acidified with 2N aqueous HCl (pH 2) and extracted with diethylether (3×100 ml). The organic extracts were combined, dried (MgSO$_4$), filtered and concentrated in vacuo to afford the desired product as a white solid (1.12 g, 87%).

$^1$HNMR (CDCl$_3$): 4.30 (t, 2H), 4.37 (t, 2H), 5.62 (2H, s), 6.99 (d, 1H), 7.37 (d, 1H).

MP 125-127° C.

Preparation 24

2-Bromo-4,6-dichlorophenol

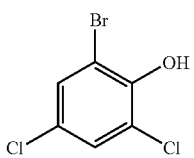

To a solution of 2,4-dichlorophenol (4 g, 24.5 mmol) and sodium acetate (2 g, 24.5 mmol) in acetic acid (40 ml) was added bromine (1.3 ml, 24.5 mmol) and the reaction stirred at room temperature for 14 hours. The reaction was poured into 600 ml ice and filtered. The product was extracted into dichloromethane (200 ml) dried over sodium sulphate and concentrated in vacuo to furnish 5.5 g of the title product as a yellow solid.

$^1$HNMR (CDCl$_3$): 5.02 (1H, s), 7.32 (1H, d), 7.42 (1H, d)

Preparation 25

1-Bromo-3,5-dichloro-2-methoxybenzene

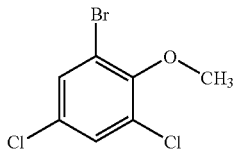

2-Bromo-4,6-dichlorophenol (Preparation 24, 4.6 g, 19 mmol), potassium carbonate (4.5 g, 32.3 mmol) and methyl iodide (1.8 ml, 20.5 mmol) were combined in 46 ml acetone and heated to reflux for 18 hours. The reaction was cooled to 0° C., 1N HCl (aqueous) was added to give pH 3, and the reaction was extracted into 50 ml ethyl acetate. The organic layer was washed with brine (2×20 ml), dried over sodium sulphate and concentrated in vacuo to afford the title compound as a brown solid (5.5 g).

$^1$HNMR (CDCl$_3$): 3.88 (3H, s), 7.35 (1H, m), 7.47 (1H, m).

Preparation 26

2-(3,5-Dichloro-2-methoxy-phenyl)-4,4,5,5-tetramethyl-[1,3,2]-dioxaborolane

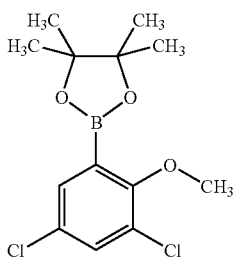

1-Bromo-3,5-dichloro-2-methoxybenzene (Preparation 25, 4.4 g, 17.5 mmol) in 95 ml diethylether was cooled to −78° C. under nitrogen. $^t$BuLi (10 ml, 35.16 mmol) was added dropwise and the reaction stirred for 15 minutes. 2-Methoxy-4,4,5,5-tetramethyl-1,3,2-dioxaborolane (4.58 g, 29 mmol) was added and the reaction stirred at −78° C. for 1 hour before pouring the reaction into 50 ml ice cold ammonium chloride (aqueous). The product was extracted with diethylether (3×30 ml), the combined organic layers were washed with water (50 ml) and brine (2×25 ml), dried over sodium sulphate, and concentrated in vacuo to afford a yellow oil. This was purified using silica gel column chromatography (heptane:ethyl acetate 9:1) to furnish a yellow oil, 4.5 g $^1$HNMR (CDCl$_3$): 1.36 (12H, s), 3.04 (3H, s), 7.45 (1H, d), 7.55 (1H, d).

Preparation 27

2,3-Dichloro-6-methoxybenzaldehyde

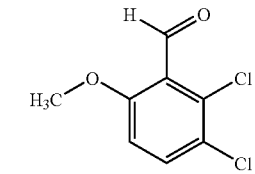

3,4-Dichloroanisole (12.5 g, 70.6 mmol) was dissolved in tetrahydrofuran (130 ml) and cooled to −76° C. n-Butyllithium (31 ml of 2.5 molar in hexanes, 77.7 mmol) was added dropwise keeping the temperature below −70° C. The solution was stirred at −70° C. for 30 minutes, then dimethylformamide (6.0 ml, 77.7 mmol) was added dropwise. The mixture was allowed to warm up to room temperature and was then poured onto ice (500 ml) and extracted with diethyl ether. The ether extracts were washed with brine then dried over anhydrous Na$_2$SO$_4$, filtered, and the solvent removed in vacuo to give the crude product. This material was stirred and heated to just below the reflux temperature in hexane (100 ml) and dichloromethane (5 ml), then cooled, and the solid filtered off to give the title compound as an off-white powder (10.0 g).

$^1$HNMR (CDCl$_3$): 3.92 (s, 3H), 6.89 (d, 1H), 7.58 (d, 1H), 10.46 (s, 1H)

MS m/z 206 [MH]−

CHN analysis: Calculated, C, 46.86%; H, 2.95%. Found, C, 47.01%; H, 3.01%.

Preparation 28

Ethyl 1-(2-methoxyethyl)-1H-pyrazole-3-carboxylate and

Ethyl 1-(2-methoxyethyl)-1H-pyrazole-5-carboxylate

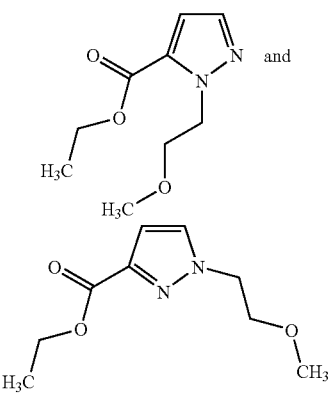

2-Methoxyethylhydrazine hydrochloride (Ref: J. Med. Chem. (1967) 11 (1) 79-83) (1.07 g, 8.5 mmol) and ethyl-4-dimethylamino-2-oxo-but-3-enoate (1.5 g, 8.5 mmol) were dissolved in ethanol (10 ml) and heated at 60° C. for 7 hours. The solvent was evaporated in vacuo and the residue was partitioned between ethyl acetate (80 ml) and dilute sodium carbonate solution (40 ml). The organic layer was dried over anhydrous $Na_2SO_4$ and the solvent removed in vacuo to give a brown gum. This material was chromatographed on silica gel (30 g) using 40% to 20% heptane in ethyl acetate. The higher running product was collected to give 2-(2-methoxyethyl)-2H-pyrazole-3-carboxylic acid ethyl ester as 750 mg of a mobile yellow oil. The lower running product was collected to give 1-(2-methoxyethyl)-1H-pyrazole-3-carboxylic acid ethyl ester as 360 mg of a yellow oil.

Data for 1-(2-methoxyethyl)-1H-pyrazole-5-carboxylic acid:

$^1$HNMR ($CDCl_3$): 1.37 (t, 3H), 3.32 (s, 3H), 3.77 (t, 2H), 4.34 (q, 2H), 4.77 (t, 2H), 6.84 (s, 1H), 7.50 (s, 1H)

MS m/z 199 [MH]+

Structures were confirmed by gHMBC (Heteronuclear Multiple Bond Correlation) and gHSQC (Homonuclear Single Quantum Coherence) NMR techniques.

Data for 1-(2-methoxyethyl)-1H-pyrazole-3-carboxylic acid:

$^1$HNMR ($CDCl_3$): 1.32 (t, 3H), 3.25 (s, 3H), 3.68 (t, 2H), 4.29 (t, 2H), 4.33 (q, 2H), 6.72 (s, 1H), 7.44 (s, 1H)

MS m/z 199 [MH]+

Preparation 29

1-(2-Methoxyethyl)-1H-pyrazole-5-carboxylic acid

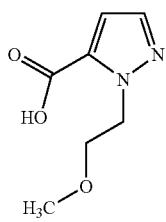

Ethyl 1-(2-methoxyethyl)-1H-pyrazole-5-carboxylate (Preparation 28, 710 mg, 3.6 mmol) was dissolved in ethanol (10 ml), a solution of sodium hydroxide (160 mg, 4.0 mmol) in water (5 ml) was added and the solution was stirred at room temperature for 2 hours. The ethanol was removed in vacuo and the residue was acidified with 2M HCl (approximately 2 ml) and extracted with dichloromethane (40 ml). The organic layers were dried over anhydrous $Na_2SO_4$, filtered and the dichloromethane removed in vacuo to give 590 mg of a pale yellow foam.

$^1$HNMR ($CDCl_3$): 3.28 (s, 3H), 3.75 (t, 2H), 4.73 (t, 2H), 6.91 (d, 1H), 7.51 (d, 1H)

MS m/z 171 [MH]+

Preparation 30

1-(2-Methoxyethyl)-1H-pyrazole-3-carboxylic acid

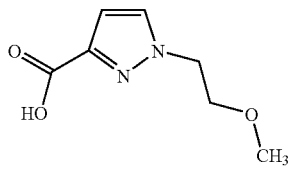

Ethyl 1-(2-methoxyethyl)-1H-pyrazole-3-carboxylate (Preparation 28, 360 mg, 1.8 mmol) was dissolved in ethanol (6 ml), a solution of sodium hydroxide (90 mg, 2.3 mmol) in water (3 ml) was added and the solution was stirred at room temperature for 3 hours. The ethanol was removed in vacuo and the residue was acidified with 2M HCl (approximately 1.5 ml), the aqueous solution was evaporated to dryness in vacuo and the residue was extracted with a mixture of dichloromethane (15 ml) and 3 drops of methanol. The mixture was filtered to remove the inorganics and the solvent removed in vacuo to give 310 mg of a yellow oil which crystallized on standing.

$^1$HNMR ($CDCl_3$): 3.33 (s, 3H), 3.78 (t, 2H), 4.40 (t, 2H), 6.86 (d, 1H), 7.54 (d, 1H)

MS m/z 171 [MH]+

The ability of the pyrazine derivatives of the formula (I) to inhibit the $Na_{V1.8}$ channel may be measured using the assay described below.

VIPR Assay for Nav1.8 Compounds

This screen is used to determine the effects of compounds on tetrodotoxin-resistant (TTX-R) sodium channels in Human Nav1.8 (HEK293) expressing cell line, utilising the technology of Aurora's fluorescent Voltage/Ion Probe Reader (VIPR). This experiment is based on FRET (Fluorescence Resonance Energy Transfer) and uses two fluorescent molecules. The first molecule, Oxonol ($DiSBAC_2(3)$), is a highly fluorescent, negatively charged, hydrophobic ion that "senses" the trans-membrane electrical potential. In response to changes in membrane potential, it can rapidly redistribute between two binding sites on opposite sides of the plasma membrane. The voltage dependent redistribution is transduced into a ratiometric fluorescent readout via a second fluorescent molecule (Coumarin (CC2-DMPE)) that binds specifically to one face of the plasma membrane and functions as a FRET partner to the mobile voltage-sensing ion. To enable the assay to work, the channels have to be pharmacologically held in the open state. This is achieved by treating the cells with either deltamethrin (for $Na_{v1.8}$) or veratridine (for the SHSY-5Y assay for TTX-S channels).

Cell Maintenance:

Human Nav1.8 cells are grown in T225 flasks, in a 5% CO2 humidified incubator to about 70% confluence. Media composition consists of DMEM/F-12, 10% FCS and 300 μg/ml Geneticine. They are split using cell dissociation fluid 1:5 to 1:20, depending on scheduling needs, and grown for 3-4 days before the next split.

Protocol:

Day One:

Plate-out HEK-Nav1.8 cells (100 μl per well) into poly-D-lysine coated plates prior to experimentation as follows: —24 hours @ $3.5 \times 10^4$ cells/well ($3.5 \times 10^5$ cells/ml) or using the technology of Select.

Day Two: VIPR Assay:

1. Equilibrate buffers at room temperature for 2 hours or at 37° C. for 30 minutes prior to experimentation.

2. Prepare Coumarin dye (see below) and store in dark. Prime with the plate washer with Na+ Free buffer and wash cells twice, Note: Plate washer deposits ~30 μl residual buffer per well. Add 100 μL Coumarin (CC2-DMPE) solution (see below) to cells and incubate for 45 minutes at room temperature avoiding bright light.

3. Prepare Oxonol ($DiSBAC_2(3)$) dye (see below):

4. Aspirate off Coumarin solution from the cells by washing in Na+ Free buffer.

5. Add 30 μl compound then add 30 μl Oxonol solution to the cells and incubate for 45 minutes at room temperature in the dark (total well volume ~90 μl).

6. Once the incubation is complete, the cells are ready to be assayed using the VIPR for sodium add back membrane potential.

The data was analyzed and reported as normalised ratios of intensities measured in the 460 nm and 580 nm channels. The process of calculating these ratios was performed as follows. An additional plate contained control solution with the same DisBAC2(3) concentrations as used in the cell plates, however no cells were included in the background plate. Intensity values at each wavelength were averaged for sample points 5-7 (initial) and 44-49 (final). These averages were subtracted from intensity values averaged over the same time periods in all assay wells. The initial ratio obtained from samples 3-8 (Ri) and the final ratio obtained from samples 45-50 (Rf) are defined as:

$$Ri = \frac{\left(\begin{array}{l}\text{Intensity 460 nm, samples 3-5} - \\ \text{background 460 nm, samples 3-5}\end{array}\right)}{\left(\begin{array}{l}\text{Intensity 580 nm, samples 3-5} - \\ \text{background 580 nm, samples 3-5}\end{array}\right)}$$

$$Rf = \frac{\left(\begin{array}{l}\text{Intensity 460 nm, samples 25-30} - \\ \text{background 460 nm, samples 25-30}\end{array}\right)}{\left(\begin{array}{l}\text{Intensity 580 nm, samples 25-30} - \\ \text{background 580 nm, samples 25-30}\end{array}\right)}$$

Final data are normalised to the starting ratio of each well and reported as Rf/Ri. This analysis is performed using a computerised specific programme designed for VIPR generated data.

Rf/Ri ratio values are plotted using Excel Labstats (curve fit) or analysed via ECADA to determine an IC50 value for each compound.

| Component: | Mwt/Conc": | weight/volume | 10X Conc. (mM) | 1X Conc. (mM): |
|---|---|---|---|---|
| Na+-Addback Buffer pH 7.4 (adjust with 5M NaOH) - 10X stock | | | | |
| NaCl | 58.44 | 93.5 g | 1600 | 160 |
| KCL | 74.55 | 3.35 g | 45.0 | 4.5 |
| CaCl2 | 1M solution | 20 ml | 20.0 | 2 |
| MgCl2 | 203.31 | 2.03 g | 10.0 | 1 |
| Hepes | 238.3 | 23.83 g | 100 | 10 |
| dH2O | | 1 L | | |
| Na+-Free Buffer pH 7.4 (adjust with 5M KOH) - 10X stock | | | | |
| Choline | 139.6 | 223.36 g | 1600 | 160 |
| CaCl2 | 1M solution | 1 ml | 1.0 | 0.1 |
| MgCl2 | 203.31 | 2.03 g | 10.0 | 1.0 |
| Hepes | 238.3 | 23.83 g | 100 | 10 |
| dH2O | | 1 L | | |

1X Na+ Free Buffer:- 400 ml 10X + 3600 ml dH2O
2X Na+ Free Buffer:- 100 ml 10X + 400 ml dH2O
1X Na+ Addback Buffer:- 50 ml 10X Na+ Addback + 450 ml dH2O

| | Solution Conc": | Final Assay Conc" |
|---|---|---|
| Coumarin (CC2-DMPE): For 2 plates:- First mix 220 μl Coumarin (1 mM) + 22 μl Pluronic (20%) in a tube + 22 ml 1X Na+-Free Buffer, gently vortex. | | |
| Coumarin (1 mM) | 10 μM | 10 μM |
| Oxonol (DiSBAC₂(3)): For 2 plates:- | | |
| 48 μl Oxonol (5 mM) + 120 ul Tartrazine (200 mM) 8.0 ml 2X Na+-Free Buffer 1.6 μl Deltametherin (5 mM) | Vortex Vortex Vortex | |
| Oxonol (5 mM) | 30 μM | 10 μM |
| Deltametherin (5 mM) | 1 μM | 330 nM |
| Tartrazine (200 mM) | 3 mM | 1.0 mM |

TTX-S Assay

The TTX-S assay is performed in the SHSY-5Y cell line which constitutively express a number of tetrodotoxin-sensitive voltage-gated sodium channels including $Na_{V1.2}$, $Na_{V1.3}$ and $Na_{V1.7}$. The procedure detailed above for the $Na_{V1.8}$ assay was followed with the exception that veratridine was substituted for deltamethrin in the assay as an opener of the sodium channels, at a final assay concentration of 50 μM.

Compounds of the Examples were tested in the assay described above, using an automated dissolution procedure to obtain a solution of the test compounds.

| Example No. | $Na_{V1.8}$ IC50 (μM) | TTX-S IC50 (μM) | Selectivity Ratio |
|---|---|---|---|
| 2 | 3.24 | 38.3 | 11.8 |
| 3 | 15.2 | >28.8 | >1.89 |
| 4 | 8.73 | >30.2 | >3.46 |
| 5 | 6.14 | ->26.3 | ->4.28 |
| 6 | 4.71 | >20.0 | >4.25 |
| 7 | 3.80 | 20.5 | 5.40 |
| 11 | 4.47 | >30.2 | >6.76 |
| 12 | 1.31 | 16.6 | 12.67 |
| 13 | 10.4 | >25.8 | >2.48 |
| 14 | 1.36 | 14.7 | 10.8 |
| 15 | >30.2 | >30.4 | — |
| 16 | 1.01 | >24.0 | >23.6 |
| 17 | 0.425 | 12.5 | 29.4 |
| 20 | 0.511 | 9.20 | 18.00 |
| 21 | 4.81 | 20.9 | 4.35 |
| 23 | 8.04 | >28.5 | >3.54 |
| 28 | 2.61 | 25.6 | 9.81 |
| 29 | 7.97 | >29.4 | >3.69 |
| 30 | 3.63 | >29.6 | >8.15 |

-continued

| Example No. | Na$_{V1.8}$ IC50 (µM) | TTX-S IC50 (µM) | Selectivity Ratio |
|---|---|---|---|
| 31 | 5.38 | >28.1 | >5.22 |
| 32 | 6.12 | >30.2 | >4.93 |
| 33 | >22.7 | ->30.2 | ->1.33 |
| 34 | 15.6 | ->30.2 | ->1.94 |
| 36 | 13.9 | >30.2 | >2.18 |
| 37 | >29.4 | >30.2 | — |
| 38 | >30.2 | >30.4 | — |
| 39 | 5.45 | >17.7 | >3.25 |
| 41 | 12.7 | >28.2 | >2.22 |
| 43 | >21.1 | >30.1 | ->1.43 |
| 44 | 16.5 | >27.4 | >1.67 |
| 48 | 8.06 | >30.2 | >3.75 |
| 49 | 0.629 | >13.6 | >21.6 |
| 50 | 10.3 | >29.9 | >2.90 |
| 51 | 0.964 | >21.1 | >21.89 |
| 55 | >21.5 | ->30.2 | ->1.40 |
| 56 | >26.7 | >30.2 | — |
| 57 | >28.4 | >30.2 | — |
| 58 | 9.42 | >30.2 | >3.21 |
| 59 | 7.23 | >25.9 | >3.58 |
| 60 | 7.19 | >30.2 | >4.20 |
| 62 | >30.2 | >30.2 | — |

Where replicate experiments were conducted resulting in multiple sets of data for a test compound, the data represent the average value from all replicate experiments.

Certain compounds of the Examples were also tested in the assay described above wherein a manual dissolution procedure was followed to obtain a solution of the test compounds. Data thus obtained are presented below:

| Example No. | Na$_{V1.8}$ IC50 (µM) | TTX-S IC50 (µM) | Selectivity Ratio |
|---|---|---|---|
| 1 | 0.988 | 11.2 | 11.4 |
| 14 | 0.276 | 3.49 | 12.7 |
| 18 | 0.417 | >30.0 | >72.0 |
| 7 | 3.98 | 15.1 | 3.79 |
| 19 | 4.72 | >30.0 | >6.36 |
| 20 | 0.188 | 12.5 | 66.5 |

Where replicate experiments were conducted resulting in multiple sets of data for a test compound, the data presented represent the average value from all replicate experiments.

What is claimed is:

1. A compound of formula (I):

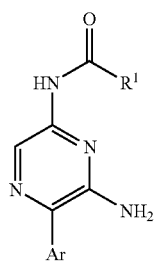

or a pharmaceutically acceptable salt thereof;
wherein R$^1$ is a 5-membered heteroaryl group comprising either (a) from 1 to 4 nitrogen atoms or (b) one oxygen or one sulphur atom and 0, 1 or 2 nitrogen atoms, optionally each independently substituted by one or more substituents selected from (C$_1$-C$_4$)alkyl, (C$_1$-C$_4$)alkoxy, halo (C$_1$-C$_4$)alkyl, (C$_1$-C$_4$)alkoxy(C$_1$-C$_4$)alkyl, amino(C$_1$-C$_4$)alkyl, amino, (C$_1$-C$_4$)alkylamino, di-((C$_1$-C$_4$)alkyl)amino, (C$_1$-C$_4$alkylamino(C$_1$-C$_4$)alkyl and di-((C$_1$-C$_4$alkyl)amino(C$_1$-C$_4$)alkyl; with the proviso that R$^1$ is not imidazolyl, oxazolyl or 1,2,4-triazolyl; Ar is

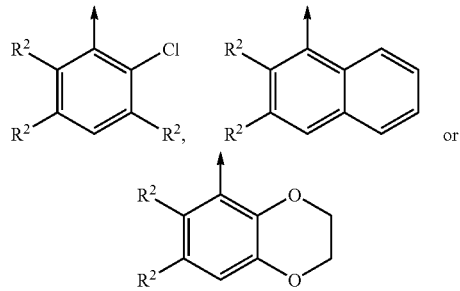

and → indicates the point of attachment to the pyrazine ring; and
each R$^2$ is independently selected from hydrogen, (C$_1$-C$_4$alkyl, (C$_1$-C$_4$alkoxy, halo(C$_1$-C$_4$)alkyl, halo(C$_1$-C$_4$alkoxy, cyano and halo.

2. A compound of formula (I), or a pharmaceutically acceptable salt thereof, according to claim 1, wherein Ar is

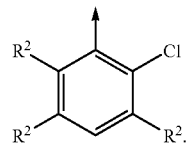

3. A compound of formula (I), or a pharmaceutically acceptable salt thereof, according to claim 1, wherein each R$^2$ is independently selected from hydrogen, methoxy, ethoxy, cyano, methyl, ethyl, trifluoromethyl, trifluomethoxy, chloro and fluoro.

4. A compound of formula (I), or a pharmaceutically acceptable salt thereof, according to claim 1, wherein each R$^2$ is independently selected from hydrogen, methoxy, cyano, trifluoromethyl, chloro and fluoro.

5. A compound of formula (I), or a pharmaceutically acceptable salt thereof, according to claim 1, wherein Ar is 2-chlorophenyl, 2,3-dichlorophenyl, 2,5-dichlorophenyl, 2,5-dichloro-3-methoxyphenyl, 2,3,5-trichlorophenyl, 2-chloro-5-methoxyphenyl, 2,3-dichloro-5-methoxyphenyl or 2-chloro-5-cyanophenyl.

6. A compound of formula (I), or a pharmaceutically acceptable salt thereof, according to claim 1, wherein R$^1$ is pyrazolyl or isoxazolyl, each being optionally substituted with (C$_1$-C$_4$)alkyl or (C$_1$-C$_4$)alkoxy(C$_1$-C$_4$)alkyl.

7. A compound of formula (I), or a pharmaceutically acceptable salt thereof, according to claim 1, wherein R$^1$ is pyrazolyl or isoxazolyl, each being substituted with one, two or three substituents independently selected from methyl, ethyl, and isopropyl.

8. A compound of formula (I), or a pharmaceutically acceptable salt thereof, according to claim 1, wherein R$^1$ is 3-methylisoxazol-4-yl, 1-methyl-1H-pyrazol-5-yl, 5-isopropylisoxazol-4-yl, 5-methylisoxazol-4-yl or 3-ethyl-5-methyl-isoxazol-4-yl.

9. A compound of formula (I) according to claim 1, selected from:

N-[6-amino-5-(2,3-dichlorophenyl)pyrazin-2-yl]-3-methylisoxazole-4-carboxamide;

N-[6-amino-5-(2,5-dichlorophenyl)pyrazin-2-yl]-3-methylisoxazole-4-carboxamide;

N-[6-amino-5-(2,5-dichloro-3-methoxyphenyl)pyrazin-2-yl]-3-methylisoxazole-4-carboxamide;

N-[6-amino-5-(2,3-dichloro-5-methoxyphenyl)pyrazin-2-yl]-1-methyl-1H-pyrazole-5-carboxamide;

N-[6-amino-5-(2-chlorophenyl)pyrazin-2-yl]-5-isopropylisoxazole-4-carboxamide;

N-[6-amino-5-(2-chlorophenyl)pyrazin-2-yl]-3-methylisoxazole-4-carboxamide;

N-[6-amino-5-(2,3,5-trichlorophenyl)pyrazin-2-yl]-5-methylisoxazole-4-carboxamide;

N-[6-amino-5-(2-chloro-5-methoxyphenyl)pyrazin-2-yl]-3-methylisoxazole-4-carboxamide;

N-[6-amino-5-(2-chloro-5-cyanophenyl)pyrazin-2-yl]-1-methyl-1H-pyrazole-5-carboxamide;

N-[6-amino-5-(2-chloro-5-methoxyphenyl)pyrazin-2-yl]-3-ethyl-5-methylisoxazole-4-carboxamide;

N-[6-amino-5-(2-chloro-5-methoxyphenyl)pyrazin-2-yl]-1-methyl-1H-pyrazole-5-carboxamide;

N-[6-amino-5-(2,5-dichlorophenyl)pyrazin-2-yl]-1-methyl-1H-pyrazole-5-carboxamide; and N-[6-amino—5-(2-chloro-5-methoxyphenyl)pyrazin-2-yl]-5-isopropylisoxazole-4-carboxamide;

or a pharmaceutically acceptable salt.

10. A pharmaceutical composition including a compound of the formula (I) or a pharmaceutically acceptable salt thereof, according to claim 1, together with one or more pharmaceutically acceptable excipients.

* * * * *